(12) United States Patent
Wang et al.

(10) Patent No.: US 11,718,611 B2
(45) Date of Patent: Aug. 8, 2023

(54) BENZENESULFONYLBENAZAMIDE COMPOUND FOR INHIBITING BCL-2 PROTEIN AND COMPOSITION AND USE THEREOF

(71) Applicant: Shenzhen TargetRx, Inc., Guangdong (CN)

(72) Inventors: Yihan Wang, Guangdong (CN); Zhiqiang Liu, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 284 days.

(21) Appl. No.: 16/625,025

(22) PCT Filed: Jun. 25, 2018

(86) PCT No.: PCT/CN2018/092588
§ 371 (c)(1),
(2) Date: Dec. 20, 2019

(87) PCT Pub. No.: WO2019/001383
PCT Pub. Date: Jan. 3, 2019

(65) Prior Publication Data
US 2020/0216442 A1    Jul. 9, 2020

(30) Foreign Application Priority Data
Jun. 26, 2017    (CN) .......................... 201710493544.X

(51) Int. Cl.
| C07D 471/04 | (2006.01) |
| A61K 31/496 | (2006.01) |
| A61P 35/00 | (2006.01) |
| A61P 35/02 | (2006.01) |

(52) U.S. Cl.
CPC .................................. C07D 471/04 (2013.01)

(58) Field of Classification Search
CPC  C07D 471/04; A61K 31/496; C07B 2200/05; C07B 59/002; A61P 35/00; A61P 35/02
See application file for complete search history.

(56) References Cited

U.S. PATENT DOCUMENTS

| 9,303,025 | B2 * | 4/2016 | Bruncko | .................. A61P 43/00 |
| 2011/0124628 | A1 | 5/2011 | Bruncko et al. | |
| 2012/0129853 | A1 | 5/2012 | Elmore et al. | |
| 2018/0065961 | A1 | 3/2018 | Catron et al. | |
| 2018/0354952 | A1 | 12/2018 | Tao et al. | |
| 2019/0225607 | A1 * | 7/2019 | Tung | ..................... C07B 59/002 |

FOREIGN PATENT DOCUMENTS

| CN | 103328474 A | 9/2013 |
| CN | 105026394 A | 11/2015 |
| JP | 2013-527202 A | 6/2013 |
| JP | 2013-543896 A | 12/2013 |
| WO | WO 2012/071336 A1 | 5/2012 |
| WO | WO 2014/158528 A1 | 10/2014 |
| WO | WO 2018/009444 A1 | 1/2018 |

OTHER PUBLICATIONS

RN2172610-82-9, registry database compound, Feb. 1, 2018.*
R2172610-52-3, registry database compound, Feb. 1, 2018.*
Tung et al., caplus an 2018:60751, 2018.*
(Continued)

*Primary Examiner* — Sun Jae Yoo
(74) *Attorney, Agent, or Firm* — Wolf, Greenfield & Sacks, P.C.

(57) ABSTRACT

An N-benzenesulfonylbenzamide compound represented by the formula (I), or a crystal form, a prodrug, pharmaceutically acceptable salts, a stereoisomer, a solvate or a hydrate thereof, a pharmaceutical composition containing same, and a use thereof as a Bcl-2 protein inhibitor for preparing a medicament for treatment of leukemia or a cancer.

(I)

8 Claims, No Drawings

(56) References Cited

OTHER PUBLICATIONS

EP 18824477.6, Apr. 28, 2020, Extended European Search Report.
[No Author Listed], Pubchem Compound for CID 91971911. Nov. 2, 2015. 6 pages.
[No Author Listed], STN Registry 1257051-06-01. STN entry date Dec. 19, 2010. 2 pages.
English Translation of First Office Action for Chinese Patent Application No. 201911104054.1, dated Jun. 3, 2020.
Wenfeng et al., Application of deuteration in drug research. Qilu Pharmaceutical Affairs. Dec. 31, 2010; 29(11):682-684.
International Search Report and Written Opinion for Application No. PCT/CN2018/092588, dated Sep. 30, 2018.
International Preliminary Report on Patentability for Application No. PCT/CN2018/092588, dated Jan. 9, 2020.
Japanese Office Action for Application No. 2020-520706, dated Apr. 6, 2020.
Extended European Search Report for Application No. EP 18824477.6, dated Apr. 28, 2020.
[No Author Listed] Database PubChem Compound CID 91971911. US National Library of Medicine. Nov. 2, 2015. 6 pages.

* cited by examiner

BENZENESULFONYLBENAZAMIDE COMPOUND FOR INHIBITING BCL-2 PROTEIN AND COMPOSITION AND USE THEREOF

CROSS REFERENCE TO RELATED APPLICATIONS

The present application is a national application of PCT/CN2018/092588 filed on Jun. 25, 2018, which claims the priority of the Chinese Patent Application No. 201710493544.X filed on Jun. 26, 2017. The Chinese Patent Application No. 201710493544.X is incorporated herein by reference as part of the disclosure of the present application.

FIELD OF THE INVENTION

The present disclosure relates to the field of pharmaceutical technology. Particularly, the present disclosure relates to the N-benzenesulfonylbenzamide compounds that have excellent inhibitory effects on Bcl-2 protein, pharmaceutical compositions comprising the same, and preparation methods and use thereof.

BACKGROUND OF THE INVENTION

Designing and synthesizing new anti-tumor drugs for tumor-specific targets have become the focus of targeted anti-tumor therapy. Recent studies have shown that the mechanism of apoptosis (programmed cell death) is involved in the tumorigenesis, development and regression of tumors. Apoptosis is highly conserved, and similar molecular mechanisms of apoptosis exist in the organisms of different species. The known apoptotic signaling pathways include both endogenous and exogenous pathways. The mitochondrial apoptotic pathway is the endogenous pathway, and the death receptor-mediated apoptotic pathway is the exogenous pathway. In the endogenous pathway of apoptosis, the functional changes of mitochondria, such as the reduction of mitochondrial membrane potential, the formation of mitochondrial membrane permeability "cavity" or the opening of the "channel", leading to the release of cytochrome c, are the core features of apoptosis.

Bcl-2 family proteins (B-cell lymphoma 2 family of proteins) are the apex and core factors of the mitochondrial pathway. The Bcl-2 family proteins are divided into three subfamilies according to the functional and structural characteristics: subfamily 1 has the anti-apoptotic function, mainly including Bcl-2 (B-cell lymphoma 2), Mcl-1 (Myeloid cell leukemia 1) and Bcl-xL (B-cell lymphoma x long), etc.; subfamily 2 has the pro-apoptotic function, mainly including Bax (Bcl-2 related protein X) and Bck (Bcl-2 antagonist/killer); the other one is the pro-apoptotic subfamily 3 containing BH3 domain only (BH3-only), including Bad (Bcl-2 antagonist of cell death), Bim (Bcl-2 interacting mediator), etc. Studies have shown that 30% to 60% of prostate cancer, 70% of breast cancer, 90% of colorectal cancer, 100% of small cell carcinoma, and lymphocytic, granulocytic leukemia cells, etc., highly expressed the Bcl-2 genes and/or proteins with the anti-apoptotic effect. Therefore, there is a need to develop Bcl-2 protein inhibitors in the field of cancer therapy.

It has been more than 10 years since the start of the research and development of Bcl-2 protein inhibitors as anticancer lead compounds, and dozens of small molecules have been discovered. However, there is only one approved Bcl-2 protein inhibitor, Venetoclax, in the international market currently. Venetoclax, a breakthrough anticancer drug jointly developed by AbbVie and Roche, was approved by the U.S. Food and Drug Administration on Apr. 11, 2016, and approved by the European Medicines Agency on Dec. 5, 2016, for the treatment of chronic lymphocytic leukemia (CLL) patients with a 17p gene deletion mutation, who have received at least one treatment.

Venetoclax is the first FDA approved Bcl-2 protein inhibitor (chemical name is 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, represented by the following formula). It is a new choice of treatment for the CLL patients with the 17p gene deletion mutation, who have a poor prognosis and limited treatment options. However, adverse reactions such as neutropenia, diarrhea, nausea, anemia, upper respiratory tract infection, thrombocytopenia and fatigue may also be found.

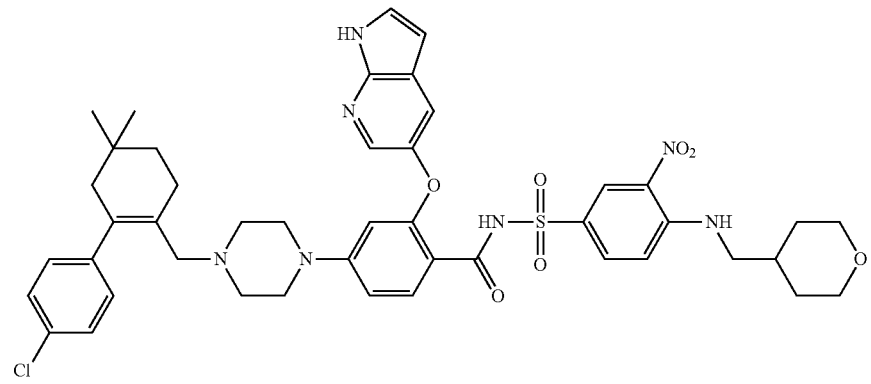

Venetoclax

Poor absorption, distribution, metabolism, and/or excretion (ADME) properties are known to be the primary causes of clinical trial failure of many drug candidates. At present, many marketed drugs have limitations on their application due to their poor ADME properties. The rapid metabolism of many drugs, which could have been effective in treating diseases, could make them difficult to be used as drugs due to their rapid removal from the body. Although a frequent or high-dose administration may solve the problem of rapid drug clearance, this approach will bring problems such as poor compliance of patients, side effects caused by high-dose administration and increased treatment costs. In addition, drugs that are rapidly metabolized may also expose the patients to undesirable toxic or reactive metabolites.

Therefore, it is still necessary to develop a Bcl-2 small molecule inhibitor with high specificity or better pharmacodynamic/pharmacokinetic properties in this field, which can selectively inhibit Bcl-2 protein, so as to restore the apoptosis process and to achieve the effect of cancer treatment.

SUMMARY OF THE INVENTION

In view of the above technical problems, the present disclosure provides a novel N-benzenesulfonylbenzamide Bcl-2 protein inhibitor, pharmaceutical composition and use thereof. More specifically, the present disclosure relates to some deuterated 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamides. These deuterated compounds have better Bcl-2 kinase inhibitory activity and/or have better pharmacodynamic/pharmacokinetic properties. In this regard, the technical solution adopted by the present disclosure is as follows:

A Bcl-2 protein inhibitor, which is an N-benzenesulfonylbenzamide compound represented by formula (I), or a pharmaceutically acceptable salt, prodrug, crystal form, stereoisomer, hydrate or solvate thereof:

deuterated drug generally retains the original biological activity and selectivity, as in the drug molecule the shape and volume of deuterium are substantially the same as those of hydrogen. At the same time, the inventors have confirmed through experiments that the binding of the carbon-deuterium bond is more stable than that of the carbon-hydrogen bond, which may directly affect the properties, such as absorption, distribution, metabolism and excretion, of some drugs, thereby improving the efficacy, safety and tolerability of the drugs.

Preferably, the content of the deuterium isotope at the deuterated position is at least greater than the natural content of the deuterium isotope (0.015%), preferably greater than 30%, more preferably greater than 50%, more preferably greater than 75%, more preferably greater than 95%, and more preferably greater than 99%.

Specifically, in the present disclosure, the content of the deuterium isotope in each deuterated position of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $X^1$ and $X^2$ is at least 5%, preferably greater than 10%, more preferably greater than 15%, more preferably greater than 20%, more preferably greater than 25%, more preferably greater than 30%, more preferably greater than 35%, more preferably greater than 40%, more preferably greater than 45%, more preferably greater than 50%, more preferably greater than 55%, more preferably greater than 60%, more preferably greater than 65%, more preferably greater than 70%,

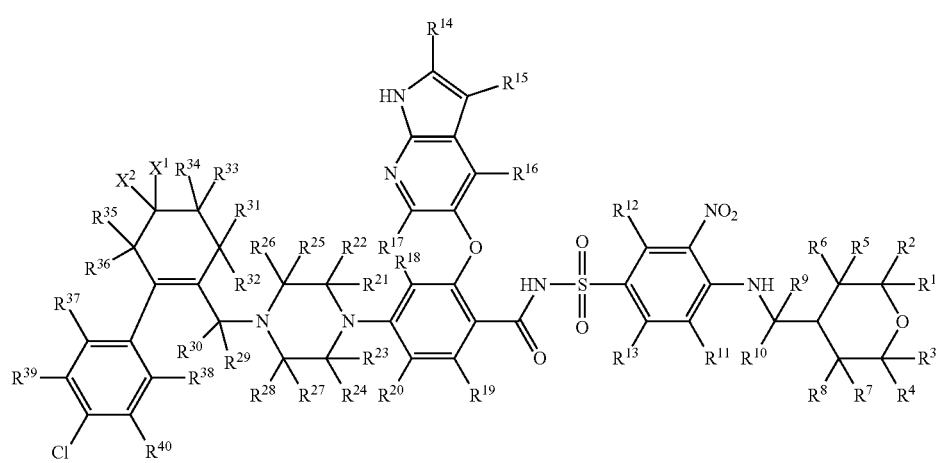

(I)

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$ and $R^{40}$ are independently selected from hydrogen, deuterium, halogen or trifluoromethyl;

$X^1$ and $X^2$ are independently selected from the group consisting of hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$; with the proviso that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18'}$ $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $X^1$ and $X^2$ is deuterated or deuterium.

With the technical solution wherein the hydrogen in the drug molecule is selectively replaced with deuterium, the more preferably greater than 75%, more preferably greater than 80%, more preferably greater than 85%, more preferably greater than 90%, more preferably greater than 95%, and more preferably greater than 99%.

Preferably, among $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $X^1$ and $X^2$ of the compound of formula (I), at least one of R/X contains deuterium, more preferably two of R/X contain deuterium, more preferably three of R/X contain deuterium, more preferably four of R/X contain deuterium, more preferably five of R/X contain deuterium, more preferably six of R/X contain deuterium, more preferably seven of R/X contain deuterium, more preferably eight of R/X contain deuterium, more preferably nine of R/X contain deuterium, more preferably ten of R/X contain deuterium, more preferably eleven of R/X contain deuterium, more preferably twelve of R/X contain deuterium, more preferably thirteen of R/X contain deuterium, more preferably fourteen of R/X contain deuterium, more preferably fifteen of R/X contain deuterium, more preferably sixteen of R/X contain deuterium, more preferably seventeen of R/X contain deuterium, more preferably eighteen of R/X contain deuterium, more preferably nineteen of R/X contain deuterium, more preferably twenty of R/X contain deuterium, more preferably twenty-one of R/X contain deuterium, more preferably twenty-two of R/X contain deuterium, more preferably twenty-three of R/X contain deuterium, more preferably twenty-four of R/X contain deuterium, more preferably twenty-five of R/X contain deuterium, more preferably twenty-six of R/X contain deuterium, more preferably twenty-seven of R/X contain deuterium, more preferably twenty-eight of R/X contain deuterium, more preferably twenty-nine of R/X contain deuterium, more preferably thirty of R/X contain deuterium, more preferably thirty-one of R/X contain deuterium, more preferably thirty-two of R/X contain deuterium, more preferably thirty-three of R/X contain deuterium, more preferably thirty-four of R/X contain deuterium, more preferably thirty-five of R/X contain deuterium, more preferably thirty-six of R/X contain deuterium, more preferably thirty-seven of R/X contain deuterium, more preferably thirty-eight of R/X contain deuterium, more preferably thirty-nine of R/X contain deuterium, more preferably forty of R/X contain deuterium, more preferably forty-one of R/X contain deuterium, more preferably forty-two of R/X contain deuterium.

As a further embodiment of the present disclosure, $R^1$, $R^2$, $R^3$, $R^4$, $R^5$, $R^6$, $R^7$ and $R^8$ are independently selected from deuterium or hydrogen.

In another preferred embodiment, $R^1$, $R^2$, $R^3$, $R^4$, $R^5$, $R^6$, $R^7$ and $R^8$ are deuterium.

As a further embodiment of the present disclosure, $R^9$ and $R^{10}$ are independently selected from deuterium or hydrogen.

In another preferred embodiment, $R^9$ and $R^{10}$ are deuterium.

As a further embodiment of the present disclosure, $R^{11}$, $R^{12}$ and $R^{13}$ are independently selected from deuterium or hydrogen.

In another preferred embodiment, $R^{11}$, $R^{12}$ and $R^{13}$ are deuterium.

As a further embodiment of the present disclosure, $R^{14}$, $R^{15}$, $R^{16}$, $R^{17}$, $R^{18}$, $R^{19}$ and $R^{20}$ are independently selected from deuterium or hydrogen.

In another preferred embodiment, $R^{14}$, $R^{15}$, $R^{16}$, $R^{17}$, $R^{18}$, $R^{19}$ and $R^{20}$ are deuterium.

As a further embodiment of the present disclosure, $R^{21}$, $R^{22}$, $R^{23}$, $R^{24}$, $R^{25}$, $R^{26}$, $R^{27}$ and $R^{28}$ are independently selected from deuterium or hydrogen.

In another preferred embodiment, $R^{21}$, $R^{22}$, $R^{23}$, $R^{24}$, $R^{25}$, $R^{26}$, $R^{27}$ and $R^{28}$ are deuterium.

As a further embodiment of the present disclosure, $R^{29}$ and $R^{30}$ are independently selected from deuterium or hydrogen.

In another preferred embodiment, $R^{29}$ and $R^{30}$ are deuterium.

As a further embodiment of the present disclosure, $R^{31}$, $R^{32}$, $R^{33}$, $R^{34}$, $R^{35}$ and $R^{36}$ are independently selected from deuterium or hydrogen.

In another preferred embodiment, $R^{31}$, $R^{32}$, $R^{33}$, $R^{34}$, $R^{35}$ and $R^{36}$ are deuterium.

As a further embodiment of the present disclosure, $R^{37}$, $R^{38}$, $R^{39}$ and $R^{40}$ are independently selected from deuterium or hydrogen.

In another preferred embodiment, $R^{37}$, $R^{38}$, $R^{39}$ and $R^{40}$ are deuterium.

As a further embodiment of the present disclosure, $R^{37}$, $R^{38}$, $R^{39}$ and $R^{40}$ are independently selected from deuterium or hydrogen.

In another preferred embodiment, $R^{37}$, $R^{38}$, $R^{39}$ and $R^{40}$ are deuterium.

As a further embodiment of the present disclosure, $X^1$ and $X^2$ are independently selected from alkyl groups substituted with one or more deuteriums.

In another preferred embodiment, $X^1$ and $X^2$ are $CD_3$.

As a further embodiment of the present disclosure, the compound is selected from the following compounds or pharmaceutically acceptable salts thereof:

(1)

-continued
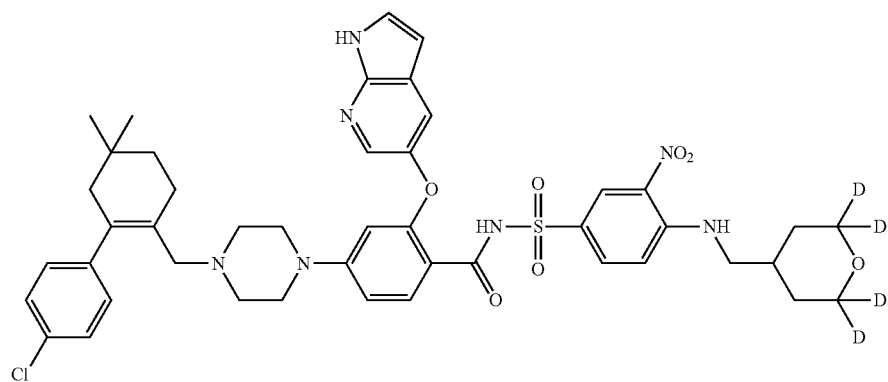
(2)
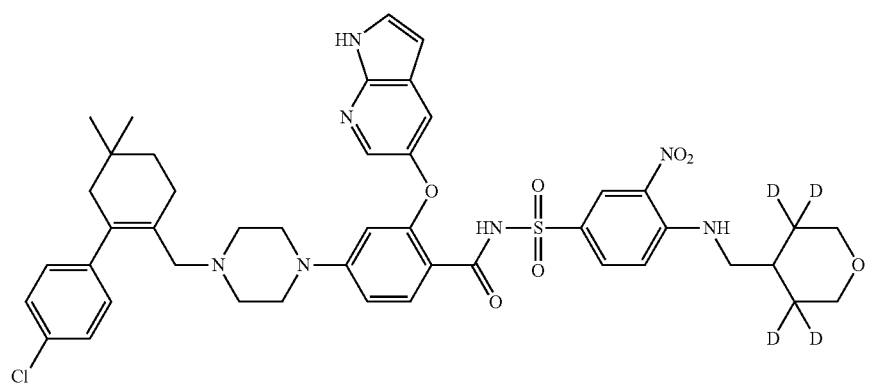
(3)
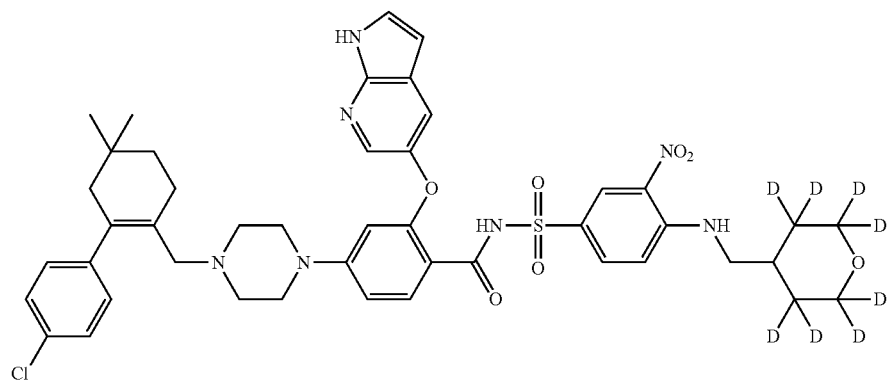
(4)
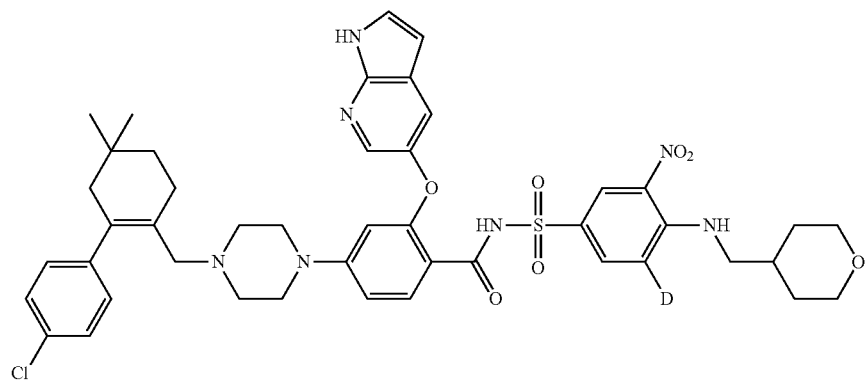
(5)

(6)
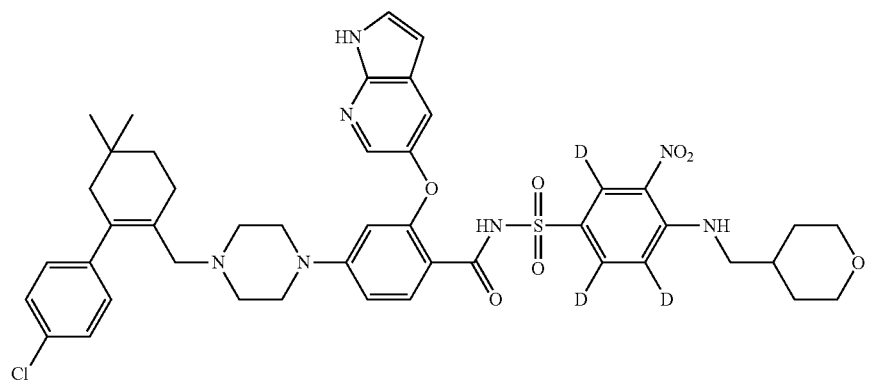
(7)
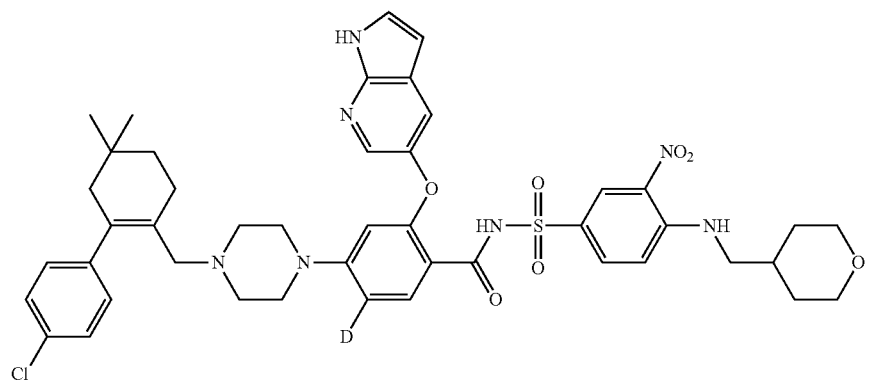
(8)
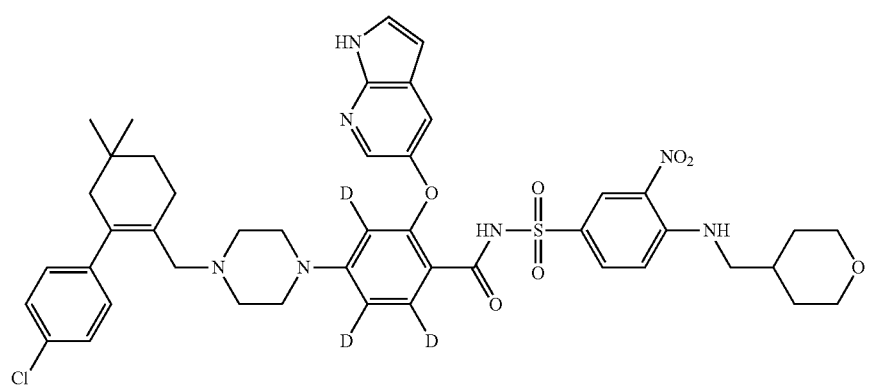
(9)
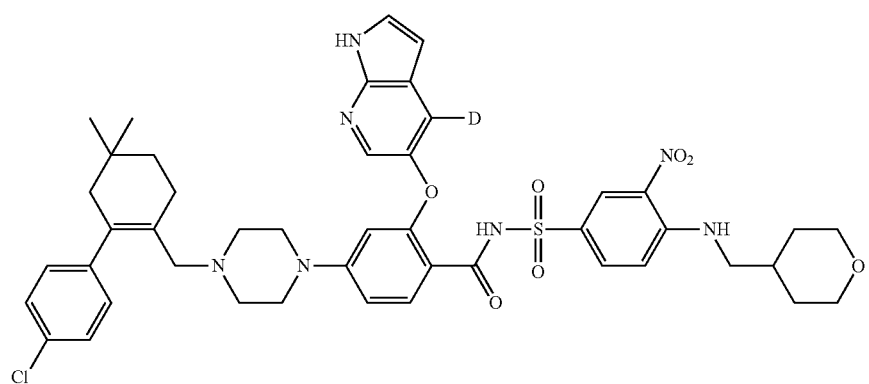

-continued
(10)
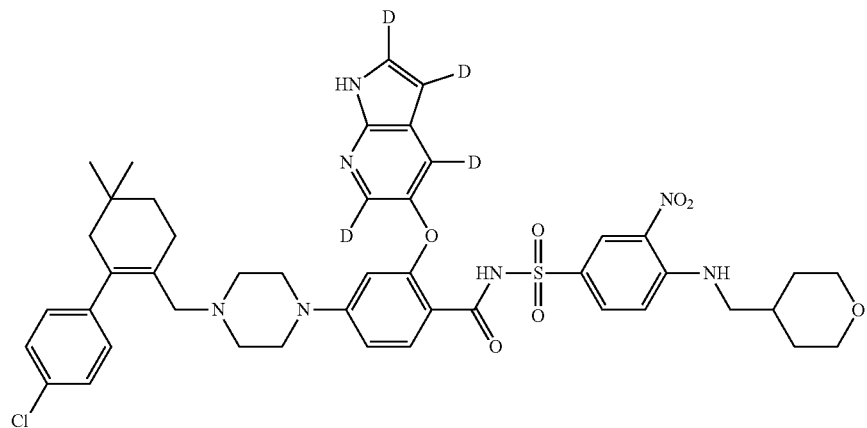
(11)
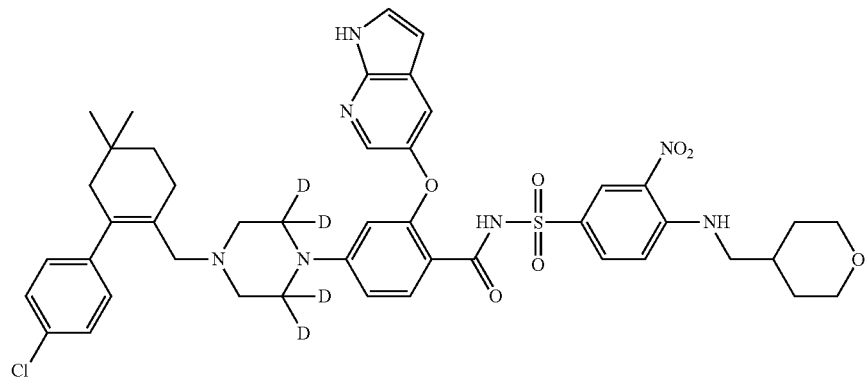
(12)
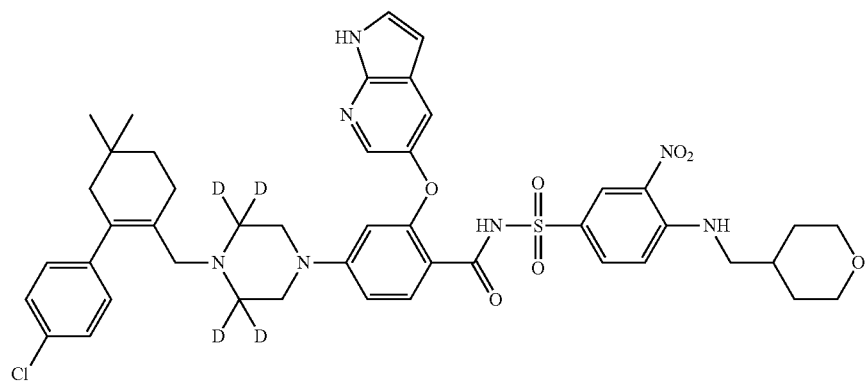
(13)
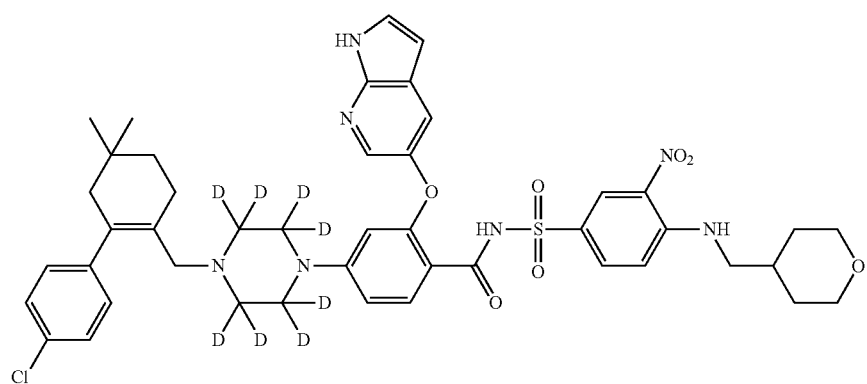

(14)
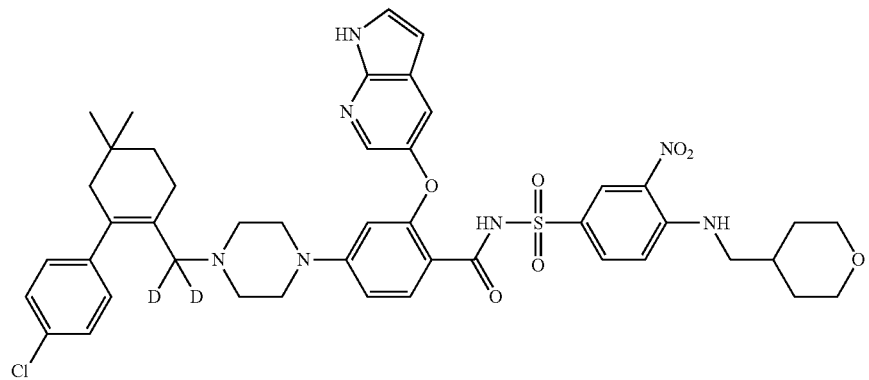
(15)
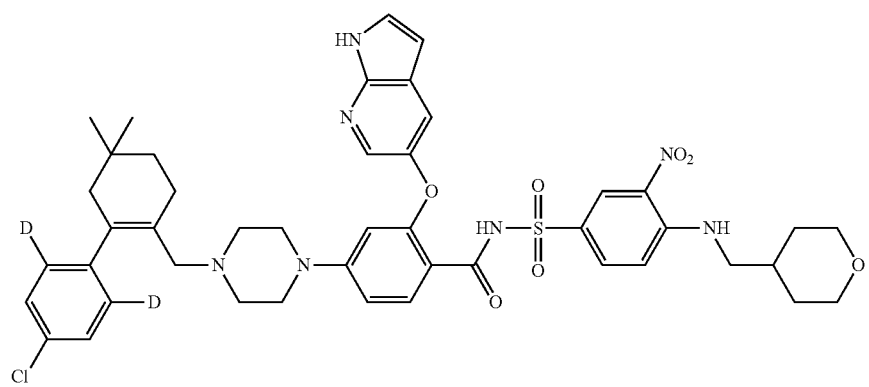
(16)
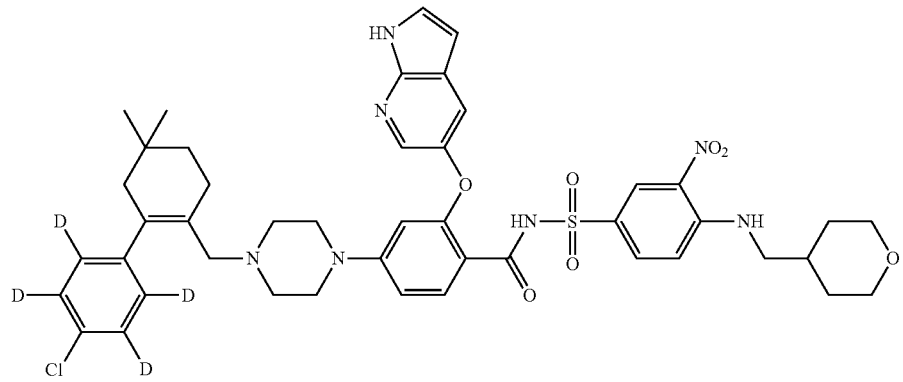
(17)
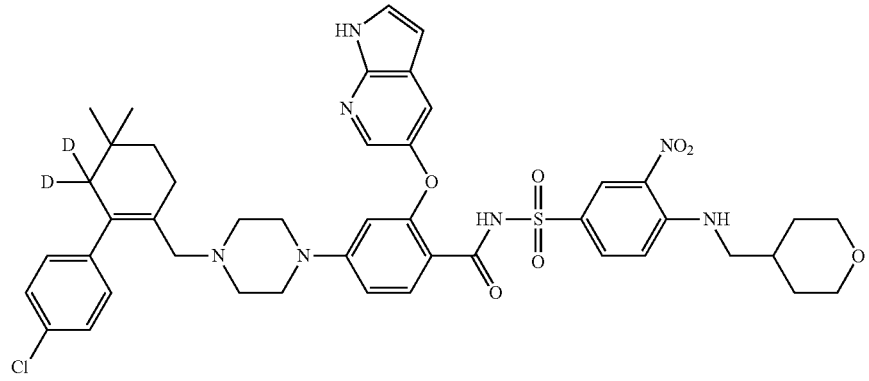

-continued
(18)
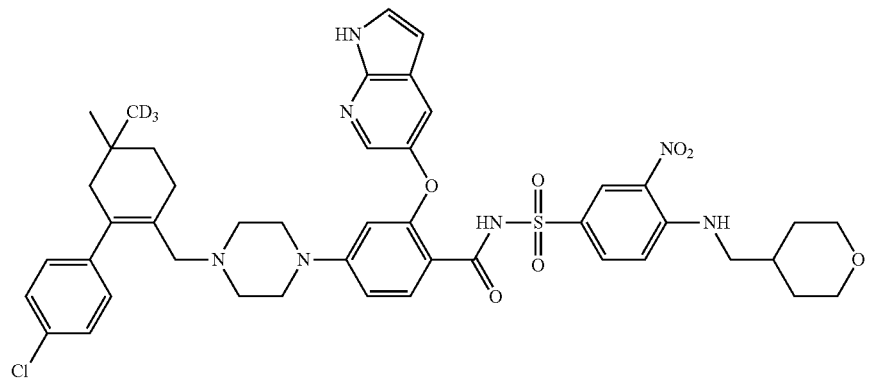
(19)
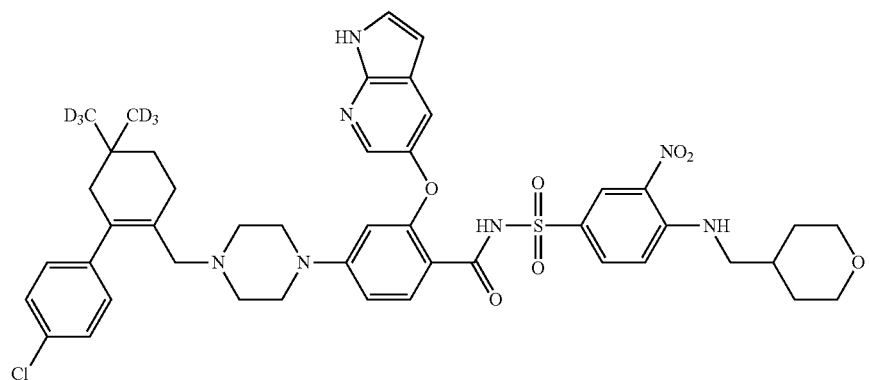
(20)
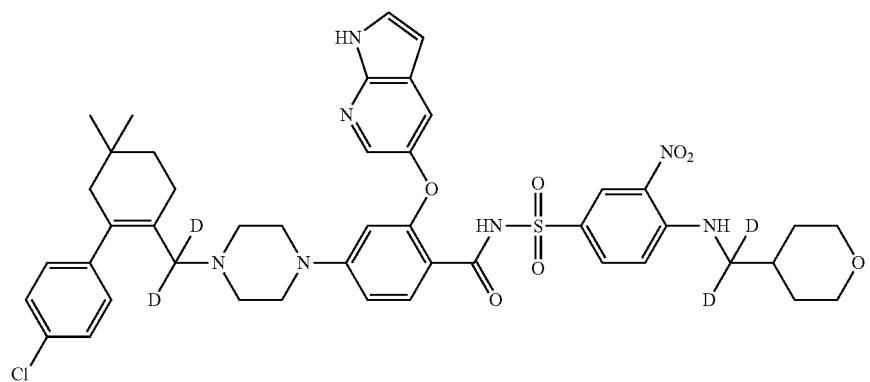
(21)
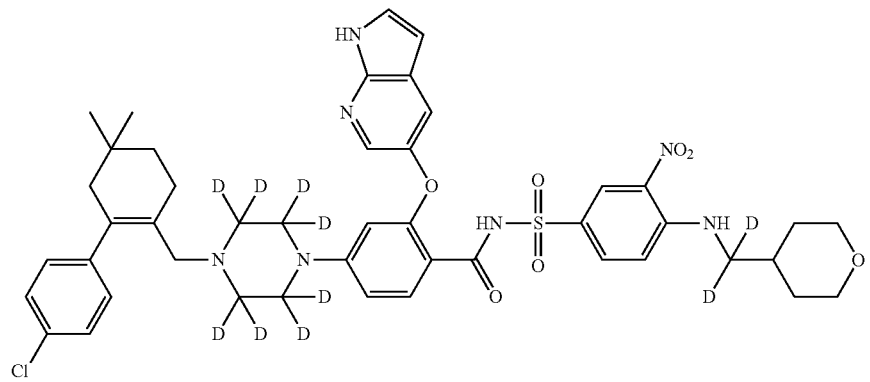

(22)
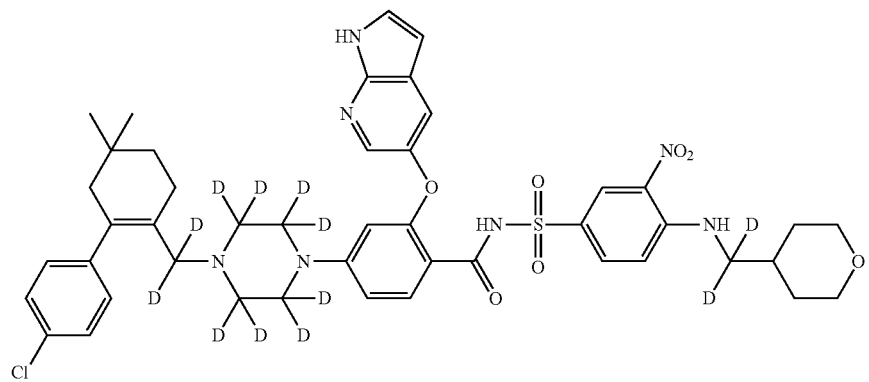
(23)
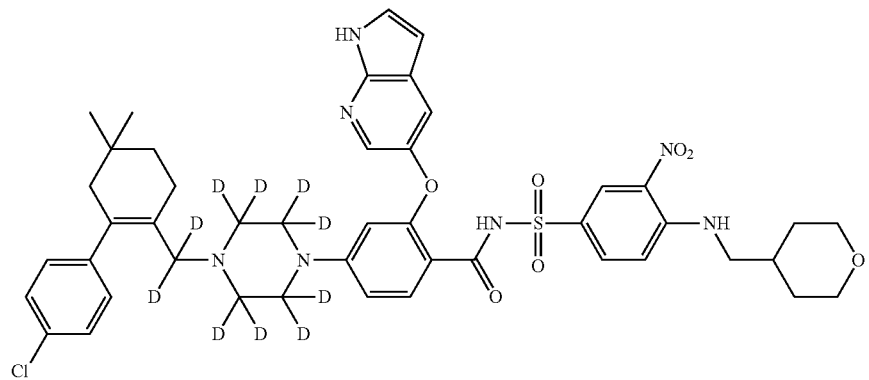
(24)
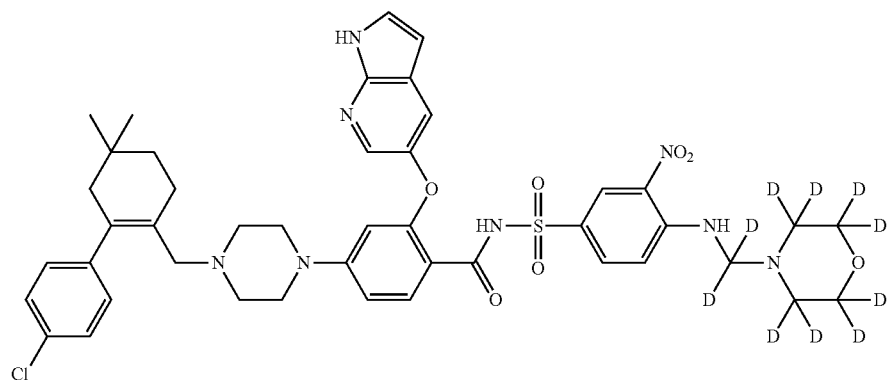
(25)
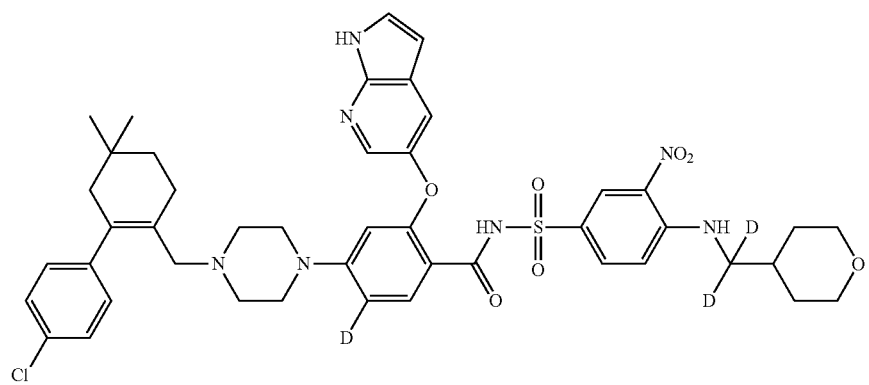

-continued
(26)
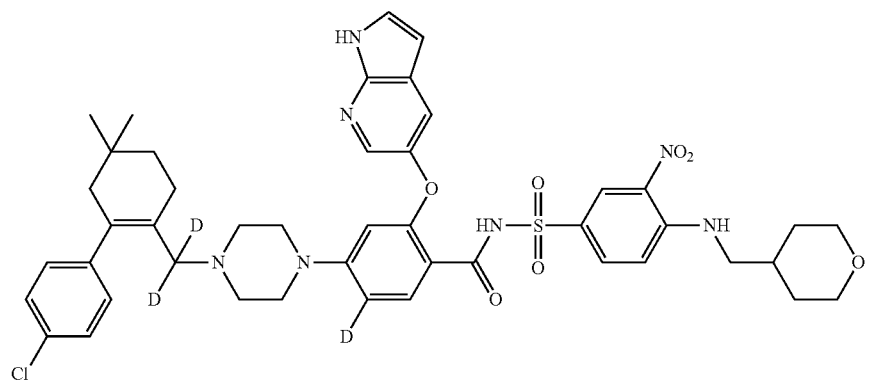
(27)
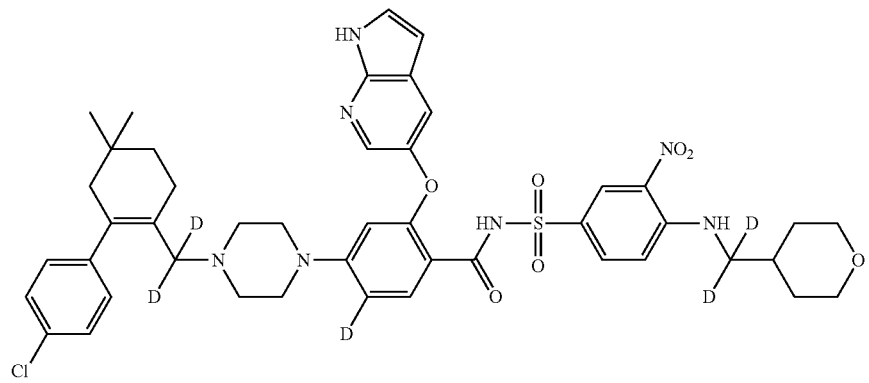
(28)
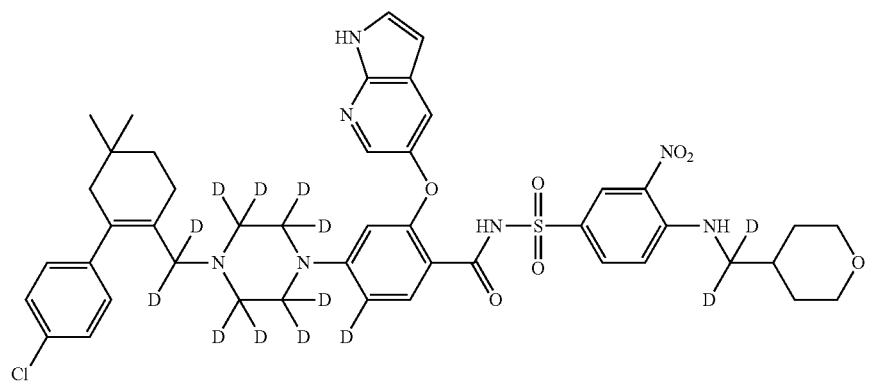
(29)
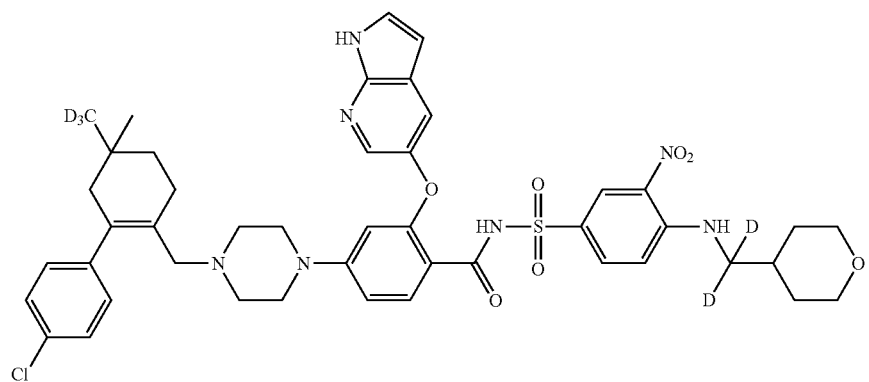

-continued
(30)
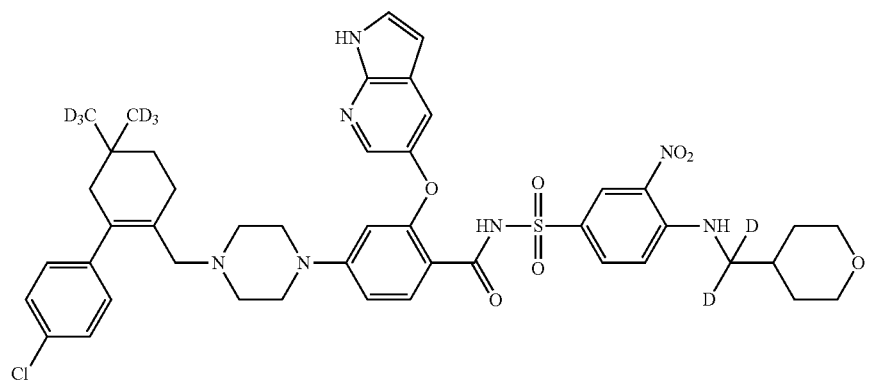
(31)
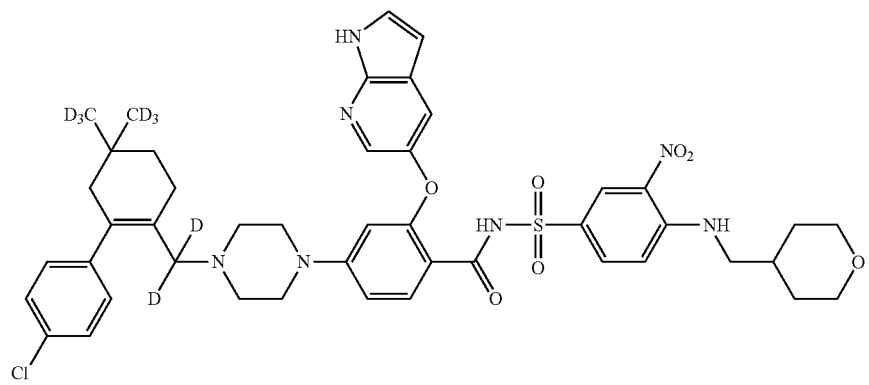
(32)
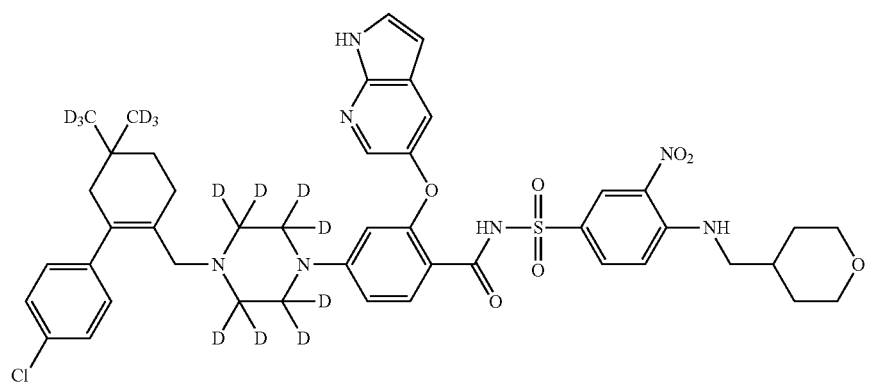
(33)
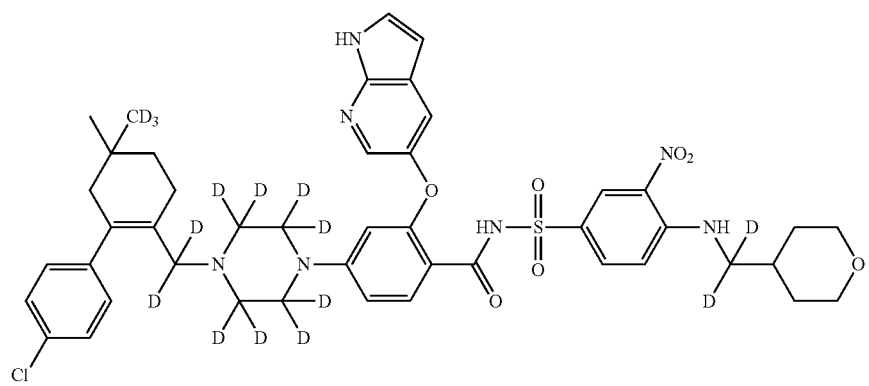

-continued

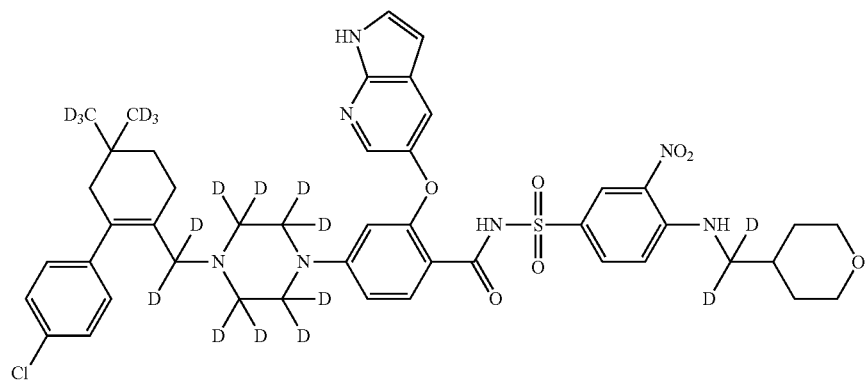
(34)

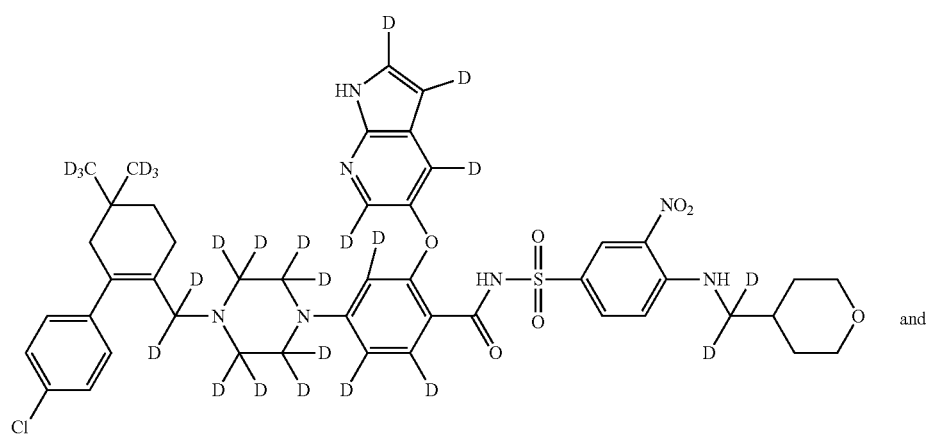
(35)
and

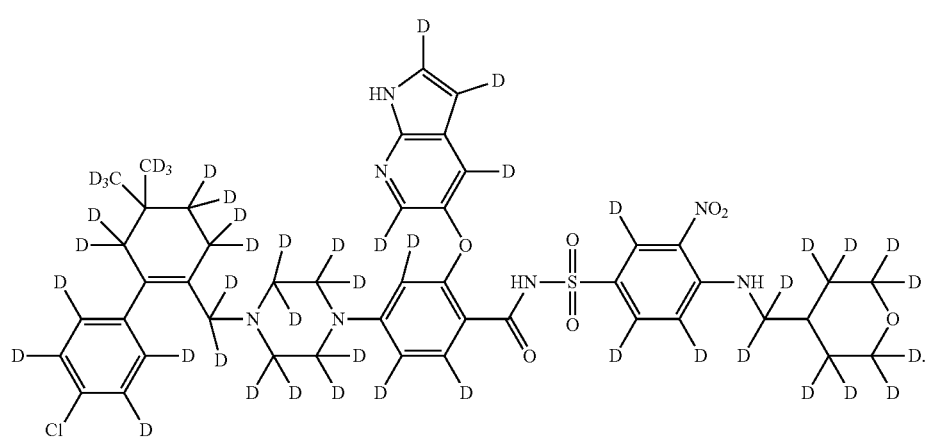
(36)

In another preferred embodiment, the compounds do not include non-deuterated compounds.

The present disclosure also provides a pharmaceutical composition, which comprises a pharmaceutically acceptable carrier and the Bcl-2 protein inhibitor described herein, or a crystal form, pharmaceutically acceptable salt, hydrate or solvent, stereoisomer, prodrug or isotope variant thereof.

As a further embodiment of the present disclosure, the pharmaceutically acceptable carrier comprises at least one of a substance or an additive, a glidant, a sweetener, a diluent, a preservative, a dye/a colorant, a flavor enhancer, a surfactant, a wetting agent, a dispersing agent, a disintegrating agent, a suspending agent, a stabilizer, an isotonic agent, a solvent or an emulsifier encapsulated in a capsule.

As a further embodiment of the present disclosure, the pharmaceutical composition is a tablet, a pill, a capsule, a powder, a granule, an ointment, an emulsion, a suspension, a solution, a suppository, an injection, an inhalant, a gel, a microsphere or an aerosol.

Typical routes of administration of the pharmaceutical compositions disclosed herein include, but are not limited to, oral, rectal, transmucosal, enteral, topical, transdermal, inhalation, parenteral, sublingual, intravaginal, intranasal, intraocular, intraperitoneal, intramuscular, subcutaneous, intravenous administration. The oral administration or injection administration is preferred.

The pharmaceutical composition disclosed herein can be produced by a method known in the art, such as a conventional mixing method, a dissolution method, a granulation method, a sugar-coating method, a pulverization method, an emulsification method, a freeze-drying method, and the like.

The present disclosure also provides a method of preparing a pharmaceutical composition comprising the steps of: mixing the pharmaceutically acceptable carrier(s) and the Bcl-2 protein inhibitors as described above, or a crystalline form, a pharmaceutically acceptable salt, a hydrate, a solvate, a stereoisomer, a prodrug or an isotopic variant.

As a further embodiment of the present disclosure, other active compounds are also included, which may be selected from: alkylating agents, angiogenesis inhibitors, antibodies, metabolic antagonists, anti-mitotic agents, anti-proliferative agents, antiviral agents, Aurora kinase inhibitors, other programmed cell death promoters (e.g., Bcl-xL, Bcl-w and Bfl-1 inhibitors), death receptor pathway activators, Bcr-Abl kinase inhibitors, BiTE (Bispecific T cell Engager) antibodies, antibody drug conjugates, biological reaction modifiers, cyclin-dependent kinase inhibitors, cell cycle inhibitors, cyclooxygenase-2 inhibitors, DADs, leukemia virus oncogene homolog (ErbB2) receptor inhibitors, growth factor inhibitors, heat shock protein (HSP)-90 inhibitors, histone deacetylase (HDAC) inhibitors, hormone therapy, immunization, inhibitors of apoptosis (IAPs), insert antibiotics, kinase inhibitors, kinesin inhibitors, Jak2 inhibitors, rapamycin inhibitors targeted to warm-blooded animals, microRNAs, mitogen-activated extracellular signal-regulated kinase inhibitors, multivalent binding proteins, NSAIDs, poly ADP (adenosine diphosphate)-ribose polymerase (PARP) inhibitors, platinum chemotherapy, polo-like kinase (Plk) inhibitors, phosphoinositide-3 kinase (PI3K) inhibitors, proteosome inhibitors, purine analogues, pyrimidine analogues, receptor tyrosine kinase inhibitors, ergotamine tartrate alkaloids (etinoids)/rhizoma sparganii alkaloids (deltoids), small inhibitory ribonucleic acids (siRNAs), topoisomerase inhibitors, ubiquitin ligase inhibitors, chemotherapeutic agents, etc.

The active ingredients disclosed herein may also be used in combination with other active ingredients. The choice of such combination is based on the condition of the treatment, the cross-reactivity of the ingredients, and the combined pharmaceutical properties. It is also possible to administer any of the compounds disclosed herein in combination with one or more other active ingredients to a patient simultaneously in a single dosage form or sequentially. Combination therapies can be administered in a regimen of simultaneous or sequential administration. When administered sequentially, the combination can be administered in two or more administrations. Combination therapy may provide "synergism" or "synergistic effects", in other words, when the active ingredients are used together, the effect obtained is greater than the sum of the effects obtained by using the compounds separately. When the active ingredients are: (1) co-formulated and administered, or delivered simultaneously in a combined formulation; (2) administered alternately or parallel as separate formulations; or (3) administered by some other regimens, synergistic effects may be obtained.

When delivered in an alternate therapy, synergistic effects may be obtained when the compounds are administered or released sequentially, for example, as separate tablets, pills or capsules, or by separate injections of separate syringes. Generally, during an alternate therapy, the effective dose of each active ingredient is administered sequentially, i.e., successively, while in a combination therapy, the effective doses of two or more active ingredients are administered together.

The present disclosure also provides the use of the Bcl-2 protein inhibitor described herein or the pharmaceutical composition thereof, which includes the use of treating bladder cancer, brain cancer, breast cancer, bone marrow cancer, cervical cancer, chronic lymphocytic leukemia, colorectal cancer, esophageal cancer, hepatocellular carcinoma, primordial lymphocytic leukemia, follicular lymphoma, lymphoma of T-cell or B-cell origin, melanoma, granulocytic leukemia, myeloma, oral cavity tumor, ovarian cancer, non-small cell lung cancer, prostate cancer, small cell carcinoma or spleen cancer.

It is to be understood that within the scope disclosed herein, the above various technical features and various technical features specifically described hereinafter (as in the examples) in the present disclosure may be combined with each other to constitute a new or preferred technical solution. Due to space limitations, we will not repeat them here.

As used herein, unless otherwise specified, "halogen" refers to F, Cl, Br, and I. More preferably, a halogen atom is selected from the group consisting of F, Cl and Br.

As used herein, unless otherwise specified, "deuterated" means that one or more hydrogens in a compound or group are substituted by deuterium; the "deuterated" may be mono-substituted, di-substituted, poly-substituted or fully-substituted by deuterium. The terms "substituted with one or more deuteriums" and "substituted one or more times by deuterium" are used interchangeably.

As used herein, unless otherwise specified, "non-deuterated compound" refers to a compound containing deuterium in a ratio that is not higher than the natural content of deuterium isotope (0.015%).

Also disclosed herein are isotopically labeled compounds (also referred to as "isotopic variants") to the extent of the original compounds disclosed herein. Examples of isotopes that can be listed in compounds disclosed herein include hydrogen, carbon, nitrogen, oxygen, phosphorus, sulfur, fluorine, and chlorine isotopes, such as $^2$H, $^3$H, $^{13}$C, $^{14}$C, $^{15}$N, $^{17}$O, $^{18}$O, $^{31}$P, $^{32}$P, $^{35}$S, $^{18}$F, and $^{36}$Cl, respectively. A compound of formula (I) disclosed herein containing the above isotope or other isotopic atom, or a polymorph, a pharmaceutically acceptable salt, a prodrug, a stereoisomer, an isotopic variant, a hydrate or a solvate thereof are all within the scope disclosed herein. Certain isotopically labeled compounds disclosed herein, such as the radioisotopes of $^3$H and $^{14}$C, are also among them and are useful in the tissue distribution experiments of drugs and substrates. Tritium, i.e., $^3$H, and carbon-14, i.e., $^{14}$C, are easier to prepare and detect and are the first choice for isotopes. In addition, substitution with heavier isotopes such as deuterium, i.e., $^2$H, has advantages in some therapies due to its good metabolic stability, for example, increased half-life in vivo or reduced dosage, and thus priority may be given in some cases. Isotopically-labeled compounds can be prepared using the schemes shown in the Examples by conventional methods by replacing the non-isotopic reagents with readily available isotopically labeled reagents.

The compound of formula (I) disclosed herein may exist in the form of an acid addition salt, a base addition salt or zwitterion. The salt of the compound is prepared during isolation of the compound or after purification of the compound. The acid addition salt of a compound is that derived from the reaction of the compound with an acid. For example, the present disclosure includes acetate, adipate, alginate, bicarbonate, citrate, aspartate, benzoate, besylate, bisulfate, butyrate, camphorate, camphorsulfonate, digluconate, formate, fumarate, glycerol phosphate, glutamate, hemisulphate, heptanoate, hexanoate, hydrochloride, hydrobromide, hydroiodide, lactobionate, lactate, maleate, mesitylene sulfonate, methanesulfonate, naphthalene sulfonate, nicotinate, oxalate, pamoate, pectinic acid salt, persulfate, phosphate, picrate, propionate, succinate, tartrate, thiocyanate, trichloroacetate, p-toluenesulfonate and undecanoate of the compound and a prodrug thereof. The base addition salt of a compound is that derived from the reaction of the compound with hydroxide, carbonate or bicarbonate of a cation such as lithium, sodium, potassium, calcium, magnesium and the like.

The compound disclosed herein may include one or more asymmetric centers, and thus may exist in a variety of "stereoisomer" forms, for example, enantiomeric and/or diastereomeric forms. For example, the compound disclosed herein may be in the form of an individual enantiomer, a diastereomer or a geometric isomer (e.g., cis and trans isomers), or may be in the form of a mixture of stereoisomers, including a racemic mixture and a mixture enrich in one or more stereoisomers. The isomers can be separated from the mixture by methods known to those skilled in the art, including: chiral high pressure liquid chromatography (HPLC) and formation and crystallization of a chiral salt; or preferred isomers can be prepared by asymmetric synthesis.

In certain instances, the compound disclosed herein may also exist in the form of a tautomer. Although only one type of non-localized resonant structure may be described, it is contemplated that all such forms fall within the scope disclosed herein. For example, for purine, pyrimidine, imidazole, guanidine, amidine, and tetrazole systems, enamine tautomers may be present, and all their possible tautomeric forms fall within the scope disclosed herein.

The term "polymorph" refers to the different arrangement of chemical drug molecules, which is generally presented as the existence form of the drug raw materials in the solid state. A drug may exist in a variety of crystal forms, and different crystal forms of the same drug may have different dissolution and absorption properties in vivo, thereby affecting the dissolution and release of the formulation.

The term "prodrug" refers to a compound that is converted in vivo to its active form with a medical effect by, for example, hydrolysis in blood. A prodrug is any covalently bonded carrier which, when administered to a patient, releases the compound disclosed herein in vivo. A prodrug is typically prepared by modifying a functional group of a drug that cleaves the prodrug in vivo to yield the parent compound. A prodrug includes, for example, a compound disclosed herein wherein a hydroxy, amino or mercapto group is bonded to any group which, when administered to a patient, can be cleaved to form a hydroxy, amino or mercapto group. Thus, representative examples of prodrugs include, but are not limited to, covalent derivatives of compounds of the present disclosure formed by the hydroxyl, amino or mercapto functional groups thereof with acetic acid, formic acid or benzoic acid. Further, in the case of a carboxylic acid (—COOH), an ester such as a methyl ester, an ethyl ester or the like may be used. The ester itself may be active and/or may be hydrolyzed in vivo under human body conditions. Suitable pharmaceutically acceptable in vivo hydrolysable esters include those which readily decompose in a human body to release a parent acid or its salt.

The term "solvate" refers to a complex in which a compound disclosed herein coordinates with a solvent molecule in a particular ratio. "Hydrate" refers to a complex formed by coordination of a compound disclosed herein with water.

Compared with the prior art, the present disclosure has the following beneficial effects: the compounds disclosed herein have excellent inhibitory properties against the Bcl-2 protein kinase; and the deuteration technology alters the metabolism of the compound in the organism, allowing the compound to have better pharmacokinetic parameters. In this case, the dose can be changed and a long-acting formulation can be formed to improve the applicability; the use of deuterium to replace hydrogen atoms in compounds can increase the drug concentration of the compound in animals due to its deuterium isotope effect, so as to improve the efficacy of the drug; and the replacement of hydrogen atoms in compounds with deuterium may increase the safety of the compounds due to the inhibition of certain metabolites.

DETAILED DESCRIPTION OF THE INVENTION

Compounds

The present disclosure provides an N-benzenesulfonyl-benzamide compound of formula (I), or a pharmaceutically acceptable salt, prodrug, crystal form, stereoisomer, hydrate or solvate thereof:

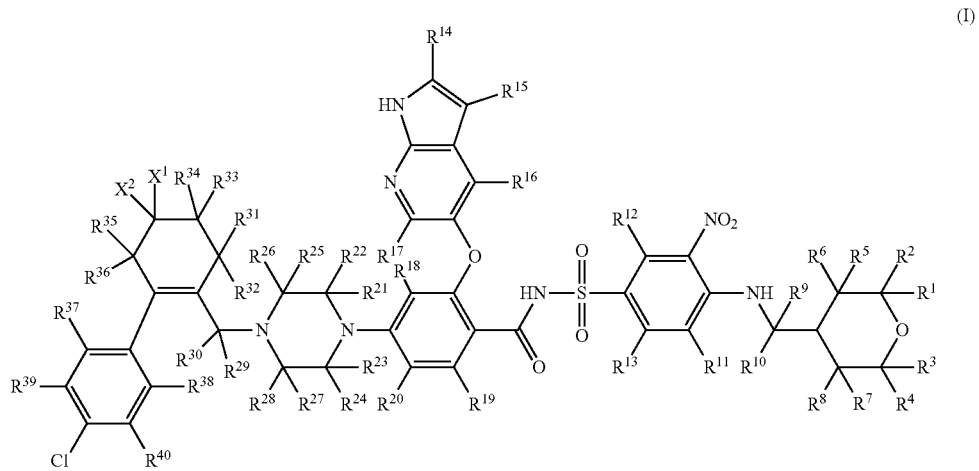

(I)

wherein, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$ and $R^{40}$ are independently selected from hydrogen, deuterium, halogen or trifluoromethyl;

$X^1$ and $X^2$ are independently selected from the group consisting of hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$;

with the proviso that at least one of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $X^1$ and $X^2$ is deuterated or deuterium.

As a preferred embodiment of the present disclosure, the content of deuterium isotope in each deuterated position is at least greater than the natural content of deuterium isotope (0.015%), preferably greater than 30%, more preferably greater than 50%, more preferably greater than 75%, more preferably greater than 95%, and more preferably greater than 99%.

In a specific embodiment, "$R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, $R^{39}$ and $R^{40}$ are independently selected from hydrogen, deuterium, halogen or trifluoromethyl" includes the technical solutions wherein, $R^1$ is selected from hydrogen, deuterium, halogen or trifluoromethyl, $R^2$ is selected from hydrogen, deuterium, halogen or trifluoromethyl, $R^3$ is selected from hydrogen, deuterium, halogen or trifluoromethyl and so on, until $R^{40}$ is selected from hydrogen, deuterium, halogen or trifluoromethyl. More specifically, the technical solutions wherein, $R^1$ is hydrogen, $R^1$ is deuterium, $R^1$ is halogen (F, Cl, Br, I), $R^1$ is trifluoromethyl, $R^2$ is hydrogen, $R^2$ is deuterium, $R^2$ is halogen (F, Cl, Br, I), $R^2$ is trifluoromethyl, $R^3$ is hydrogen, $R^3$ is deuterium, $R^3$ is halogen (F, Cl, Br, I), $R^3$ is trifluoromethyl and so on, until $R^{40}$ is hydrogen, $R^{40}$ is deuterium, $R^{40}$ is halogen (F, Cl, Br, I) and $R^{40}$ is trifluoromethyl, are included.

In another specific embodiment, "$X^1$ and $X^2$ are independently selected from the group consisting of hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$" includes the technical solutions wherein, $X^1$ is selected from hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$, and $X^2$ is selected from hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$. More specifically, the technical solutions wherein, $X^1$ is hydrogen, $X^1$ is deuterium, $X^1$ is $CH_2D$, $X^1$ is $CHD_2$, $X^1$ is $CD_3$, $X^1$ is $CH_2CH_3$, $X^1$ is $CHDCH_3$, $X^1$ is $CHDCH_2D$, $X^1$ is $CHDCHD_2$, $X^1$ is $CHDCD_3$, $X^1$ is $CD_2CH_3$, $X^1$ is $CD_2CH_2D$, $X^1$ is $CD_2CHD_2$, $X^1$ is $CD_2CD_3$, and $X^2$ is hydrogen, $X^2$ is deuterium, $X^2$ is $CH_2D$, $X^2$ is $CHD_2$, $X^2$ is $CD_3$, $X^2$ is $CH_2CH_3$, $X^2$ is $CHDCH_3$, $X^2$ is $CHDCH_2D$, $X^2$ is $CHDCHD_2$, $X^2$ is $CHDCD_3$, $X^2$ is $CD_2CH_3$, $X^2$ is $CD_2CH_2D$, $X^2$ is $CD_2CHD_2$, $X^2$ is $CD_2CD_3$, are included.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $CH_2D$, $CHD_2$ and $CD_3$, $R^1$ to $R^{10}$, $R^{21}$ to $R^{30}$ and $R^{31}$ to $R^{36}$ are as defined above, with the proviso that the compound of formula (I) contains at least one deuterium atom.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $CH_2D$, $CHD_2$ and $CD_3$, $R^1$ to $R^{10}$, $R^{21}$ to $R^{30}$ and $R^{31}$ to $R^{36}$ are independently selected from hydrogen or deuterium, with the proviso that the compound of formula (I) contains at least one deuterium atom.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl or $CD_3$, $R^1$ to $R^8$ and $R^{31}$ to $R^{36}$ are hydrogen, $R^9$ to $R^{10}$ and $R^{21}$ to $R^{30}$ are independently selected from hydrogen or deuterium, with the proviso that the compound of formula (I) contains at least one deuterium atom.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $R^1$ to $R^8$ and $R^{31}$ to $R^{36}$ are hydrogen, $R^9$ to $R^{10}$ and $R^{21}$ to $R^{30}$ are independently selected from hydrogen or deuterium, with the proviso that the compound of formula (I) contains at least one deuterium atom.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $R^1$ to $R^8$ and $R^{31}$ to $R^{36}$ are hydrogen, $R^9$ and $R^{10}$ are deuterium, $R^{21}$ to $R^{30}$ are independently selected from hydrogen or deuterium. In another specific embodiment, $R^{21}$ to $R^{28}$ are deuterium; in another specific embodiment, $R^{21}$ to $R^{28}$ are hydrogen; in another specific embodiment, $R^{29}$ to $R^{30}$ are deuterium; in another specific embodiment, $R^{29}$ to $R^{30}$ are hydrogen.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $R^1$ to $R^8$ and $R^{31}$ to $R^{36}$ are hydrogen, $R^{21}$ to $R^{28}$ are deuterium, $R^9$, $R^{10}$, $R^{29}$ and $R^{30}$ are independently selected from hydrogen or deuterium. In another specific embodiment, $R^9$ and $R^{10}$ are deuterium; in another specific embodiment, $R^{29}$ and $R^{30}$ are hydrogen; in another specific embodiment, $R^{29}$ and $R^{30}$ are deuterium.

In a preferred embodiment, the present disclosure relates to a compound of formula (I), or the pharmaceutically acceptable salt, prodrug, hydrate or solvent, crystal form, stereoisomer or isotope variant thereof, wherein, $R^{11}$ to $R^{20}$ and $R^{37}$ to $R^{40}$ are hydrogen, $X^1$ and $X^2$ are independently selected from methyl, $R^1$ to $R^8$ and $R^{31}$ to $R^{36}$ are hydrogen, $R^{29}$ and $R^{30}$ are deuterium, $R^9$ to $R^{10}$ and $R^{21}$ to $R^{28}$ are independently selected from hydrogen or deuterium. In another specific embodiment, $R^9$ to $R^{10}$ are deuterium; in another specific embodiment, $R^9$ to $R^{10}$ are hydrogen; in another specific embodiment, $R^{21}$ to $R^{28}$ are deuterium; in another specific embodiment, $R^{21}$ to $R^{28}$ are hydrogen.

In a preferred embodiment, the compound of formula (I) is selected from the compounds of the following formulae:
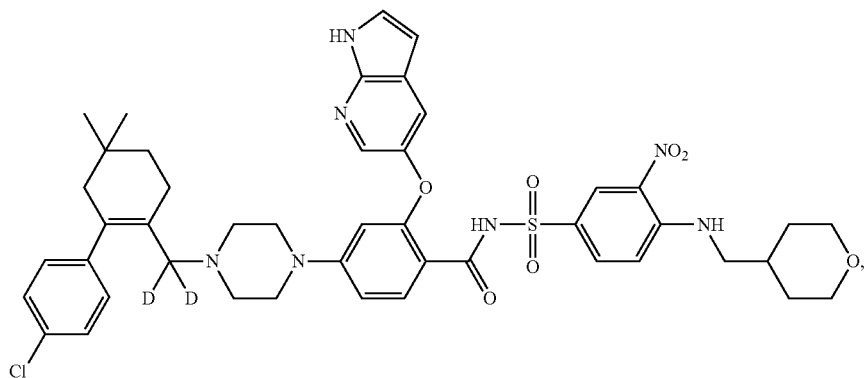
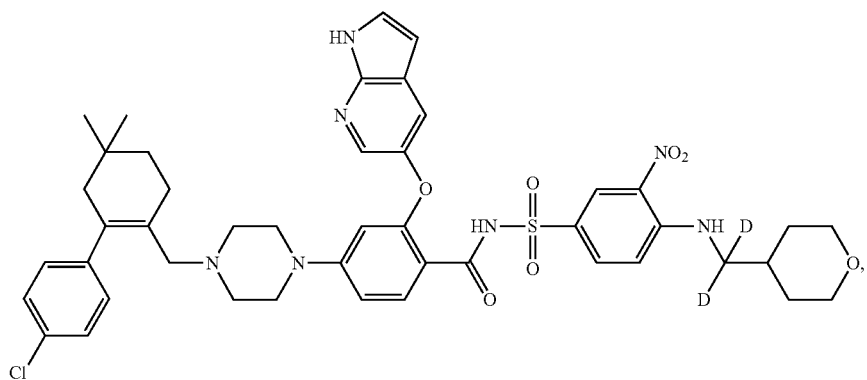
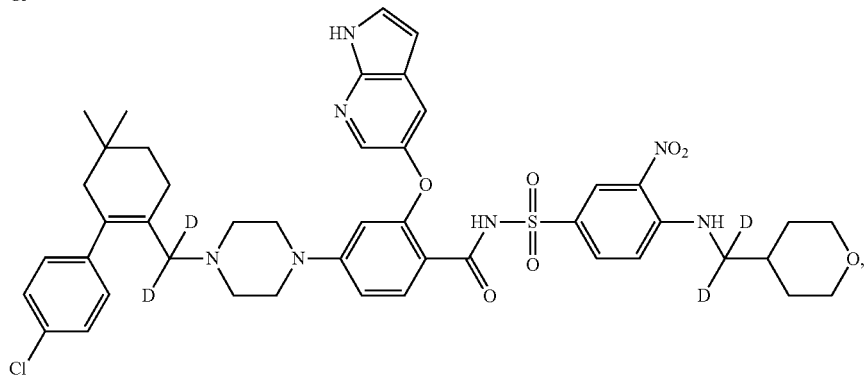
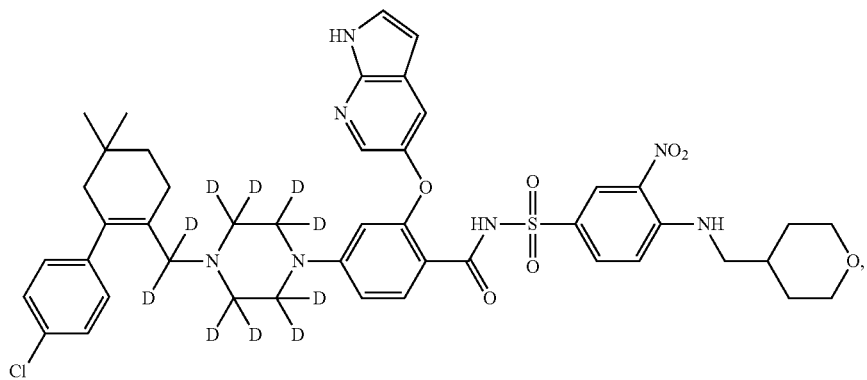

-continued

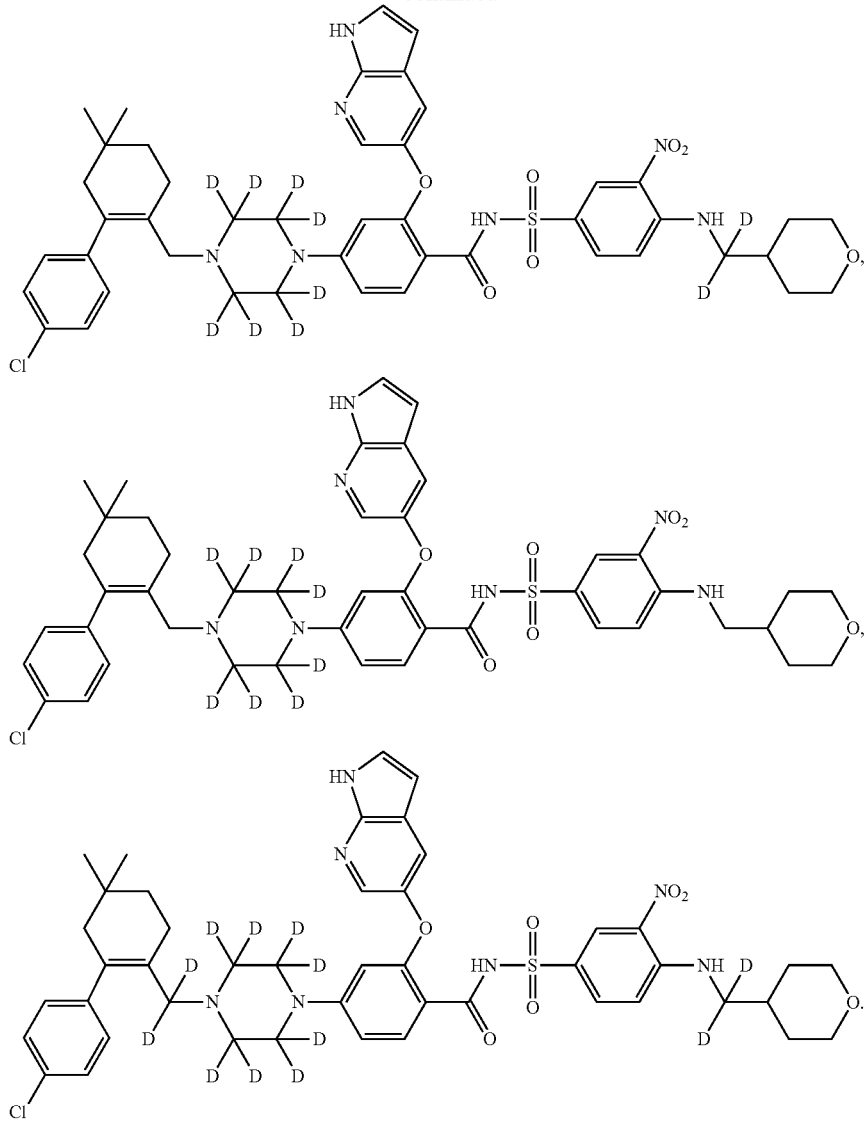

Synthesis

The compounds disclosed herein, including their salts, can be prepared using known organic synthetic techniques and can be synthesized according to any of various possible synthetic routes, such as those in the schemes below. The reaction for preparing compounds disclosed herein can be carried out in a suitable solvent, which can be easily selected by those skilled in the art of organic synthesis. Suitable solvents can be substantially unreactive with starting materials (reactants), intermediates or products at the temperature at which the reaction is carried out (for example, at temperatures ranging from the freezing temperature to boiling temperature of a solvent). A given reaction can be carried out in one solvent or a mixture of more than one solvents. The skilled person can select the solvent for the particular reaction step depending on the particular reaction step.

The preparation of the compounds disclosed herein may involve protection and deprotection of different chemical groups. One skilled in the art can readily determine the need for protection and deprotection and the choice of appropriate protecting groups. The chemical properties of protecting groups can be found, for example, in Wuts and Greene, Protective Groups in Organic Synthesis, 4th Ed., John Wiley & Sons: New Jersey, (2006), which is incorporated herein by reference in its entirety.

The reaction can be monitored according to any suitable method known in the art. For example, product formation can be monitored by spectroscopic means (such as nuclear magnetic resonance (NMR) spectroscopy (e.g., $^1$H or $^{13}$C), infrared (IR) spectroscopy, spectrophotometry (e.g., UV-visible), mass spectrometry (MS)) or by chromatographic methods (such as high performance liquid chromatography (HPLC) or thin layer chromatography (TLC)).

Pharmaceutical Compositions, Formulations and Kits

In another aspect, provided herein is a pharmaceutical composition comprising the compound disclosed herein (also referred to as "active component") and a pharmaceutically acceptable excipient. In some embodiments, the pharmaceutical composition comprises an effective amount of the active component. In some embodiments, the pharmaceutical composition comprises a therapeutically effective amount of the active component. In some embodiments, the pharmaceutical composition comprises a prophylactically effective amount of the active component.

A pharmaceutically acceptable excipient for use in the present disclosure refers to a non-toxic carrier, adjuvant or vehicle that does not destroy the pharmacological activity of the compound formulated together. Pharmaceutically acceptable carriers, adjuvants, or vehicles that can be used in the compositions disclosed herein include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based substances, polyethylene glycol, sodium carboxymethyl cellulose, polyacrylate, wax, polyethylene-polyoxypropylene block polymer, polyethylene glycol and lanolin.

The present disclosure also includes a kit (e.g., pharmaceutical packs). The kit provided may include compounds disclosed herein, other therapeutic agents, and first and second containers containing the compounds disclosed herein and other therapeutic agents (e.g., vials, ampoules, bottles, syringes, and/or dispersible packages or other suitable containers). In some embodiments, the kit provided can also optionally include a third container containing a pharmaceutically acceptable excipient for diluting or suspending compounds disclosed herein and/or other therapeutic agents. In some embodiments, the compounds disclosed herein and other therapeutic agents provided in a first container and a second container are combined to form a unit dosage form.

The pharmaceutical composition provided herein can be administered by a variety of routes including, but not limited to, oral administration, parenteral administration, inhalation administration, topical administration, rectal administration, nasal administration, buccal cavity administration, vaginal administration, administration by implant or other means of administration. For example, the parenteral administration as used herein includes subcutaneous administration, intradermal administration, intravenous administration, intramuscular administration, intra-articular administration, intra-arterial administration, intrasynovial administration, intrastemal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the condition disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc., or may be continued indefinitely, for example, for the rest of the subject's life. In some embodiments, the chronic administration is intended to provide a constant level of the compound in the blood, e.g., within the therapeutic window over the extended period of time.

The pharmaceutical compostions disclosed herein may be further delivered using a variety of dosing methods. For example, In some embodiments, the pharmaceutical composition may be given as a bolus, e.g., in order to rapidly raise the concentration of the compound in the blood to an effective level. The placement of the bolus dose depends on the systemic levels of the active ingredient desired, e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1% to about 50% by weight or preferably from about 1% to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 mg/kg to about 20 mg/kg of the compound disclosed herein, with preferred doses each providing from about 0.1 mg/kg to about 10 mg/kg, and especially about 1 mg/kg to about 5 mg/kg.

Transdermal doses are generally selected to provide similar or lower blood levels than are achieved using injection doses, generally in an amount ranging from about 0.01% to about 20% by weight, preferably from about 0.1% to about 20% by weight, preferably from about 0.1% to about 10% by weight, and more preferably from about 0.5% to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As mentioned before, the active compound in such compositions is typically a minor component, often being from about 0.05% to 10% by weight with the remainder being the injectable excipient and the like.

Transdermal compositions are typically formulated as a topical ointment or cream containing the active ingredient(s). When formulated as an ointment, the active ingredients will typically be combined with either a paraffinic or a water-miscible ointment base.

Alternatively, the active ingredients may be formulated in a cream with, for example an oil-in-water cream base. Such transdermal formulations are well-known in the art and generally include additional ingredients to enhance the stable dermal penetration of the active ingredients or formulation. All such known transdermal formulations and ingredients are included within the scope provided herein.

The compounds disclosed herein can also be administered by a transdermal device. Accordingly, transdermal administration can be accomplished using a reservoir or a patch in porous membrane type or with various solid matrixes.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds disclosed herein can also be administered in sustained release forms or from sustained release drug delivery systems. A description of representative sustained release materials can be found in Remington's Pharmaceutical Sciences.

The present disclosure also relates to the pharmaceutically acceptable formulations of a compound disclosed herein. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In some embodiments, the cyclodextrin is a sulfoalkyl ether β-cyclodextrin, e.g., for example, sulfobutyl ether 3-cyclodextrin, also known as Captisol. See, e.g., U.S. Pat. No. 5,376,645. In some embodiments, the formulation comprises hexapropyl-3-cyclodextrin (e.g., 10-50% in water).

EXAMPLES

The preparation methods of the compound of formula (I) disclosed herein are described more specifically below, but these specific methods should not be construed as limiting the scope of the present disclosure in any way. The compound of the present disclosure may also be conveniently prepared by optionally combining various synthetic methods described in the description or those known in the art, and such combinations may be readily made by those skilled in the art.

Generally, in the preparation process, the reactions are usually carried out in an inert solvent at the temperature ranging from room temperature to reflux temperature (e.g., from 0° C. to 100° C., preferably from 0° C. to 80° C.). The reaction time is usually from 0.1 to 60 hours, preferably from 0.5 to 24 hours.

Intermediate Compound 1: Synthesis of methyl 2-[(1H-pyrrolo[2,3-b]pyridin-5-yl)oxy]-4-fluorobenzoate

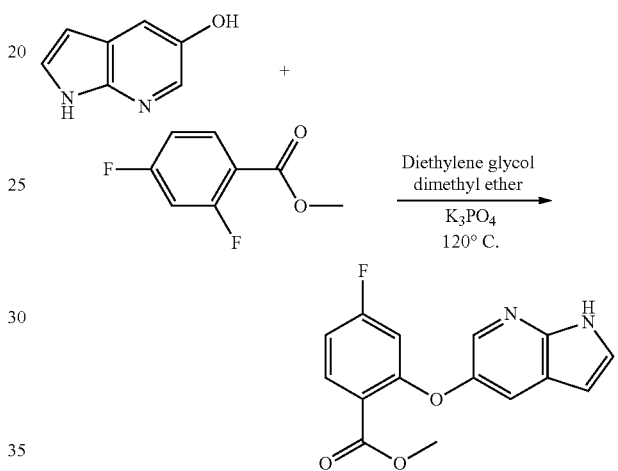

Under the nitrogen atmosphere, 1H-pyrrolo[2,3-b]pyridin-5-ol (1.0 g, 7.45 mmol), methyl 2,4-difluorobenzoate (1.6 g, 9.31 mmol) and potassium phosphate (2.05 g, 9.69 mmol) were added to 20 ml of diethylene glycol dimethyl ether successively. The reaction solution was stirred at 115° C. for about 10 h, and analyzed by plate chromatography until the material was completely consumed. The reaction solution was cooled to room temperature, quenched with water, and extracted with ethyl acetate. The organic phase was collected, and purified by column chromatography to give 1.3 g of a white solid product, with the yield of 62%. $^1$H NMR (400 MHz, CDCl$_3$) δ 10.66 (s, 1H), 8.24 (d, J=2.5 Hz, 1H), 7.99 (dd, J=8.8, 6.6 Hz, 1H), 7.69 (d, J=2.4 Hz, 1H), 7.50-7.42 (m, 1H), 6.83 (ddd, J=8.8, 7.6, 2.4 Hz, 1H), 6.57-6.49 (m, 2H), 3.93 (s, 3H).

Intermediate Compound 2: Synthesis of 4-chlorophenylboronic acid pinacol ester

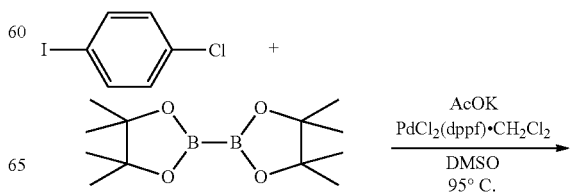

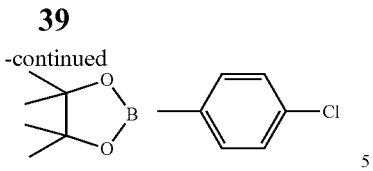

Under the nitrogen atmosphere, chloroiodobenzene (6.0 g, 25.16 mmol), Pd(dppf)Cl$_2$*CH$_2$Cl$_2$ (1.0 g, 1.26 mmol), potassium acetate (4.93 g, 50.3 mmol) and bis(pinacolato)diboron (6.4 g, 26.4 mmol) were added to 50 ml of DMSO successively, and the resulting solution was heated to 95° C. and reacted for 10 h. The reaction solution was cooled to room temperature, quenched with water, and extracted with dichloromethane. The organic phase was collected, and purified by column chromatography to give 3.2 g of a yellow solid product, with the yield of 50%. $^1$H NMR (400 MHz, CDCl$_3$) δ 7.73 (d, J=8.2 Hz, 2H), 7.35 (d, J=8.3 Hz, 2H), 1.34 (s, 12H).

Intermediate Compound 3: Synthesis of 3-nitro-4-[(tetrahydro-2H-pyran-4-ylmethyl)amino]benzenesulfonamide

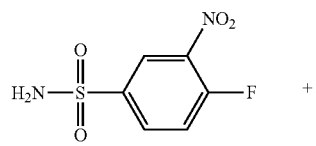

4-Fluoro-3-nitrobenzenesulfonamide (1.0 g, 4.54 mmol), (tetrahydro-2H-pyran-4-yl)methanamine (0.6 g, 4.49 mmol) and triethylamine (1.3 g, 6.81 mmol) were added to 10 ml of tetrahydrofuran successively. After stirring at room temperature for 5 h, the solvent was removed. 20 ml of methanol was added to form a slurry, and the mixture was dried to give 1.4 g of a product, with the yield of 97%. $^1$H NMR (400 MHz, DMSO-d$_6$) δ 8.59 (s, 1H), 8.47 (d, J=2.2 Hz, 1H), 7.83 (dd, J=9.2, 2.1 Hz, 1H), 7.35 (s, 2H), 7.30 (d, J=9.3 Hz, 1H), 3.85 (dd, J=11.0, 3.3 Hz, 2H), 3.37 (s, 2H), 3.26 (t, J=11.6 Hz, 2H), 1.91 (ddd, J=11.2, 7.6, 4.0 Hz, 1H), 1.61 (d, J=12.7 Hz, 2H), 1.33-1.21 (n, 2H).

Example 1 Preparation of 4-(4-{[2-(4-chlorophenyl)-4,4-dimethylcyclohex-1-en-1-yl]methyl-d$_2$}piperazin-1-yl)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, which is compound T-1, Represented by the Following Formula

T-1

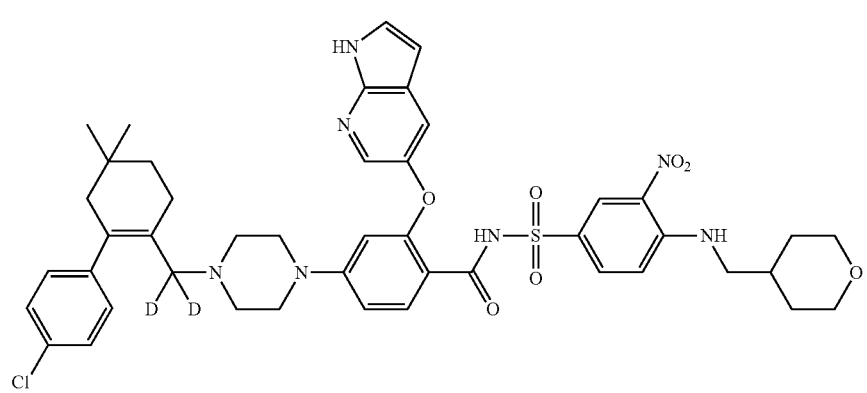

The following routes is used for synthesis:

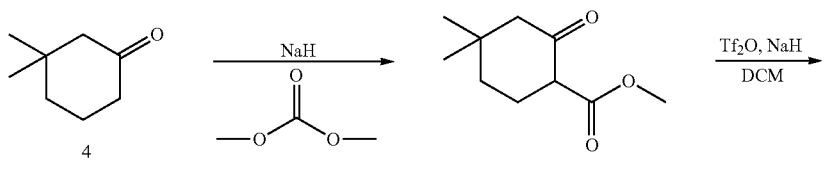

-continued
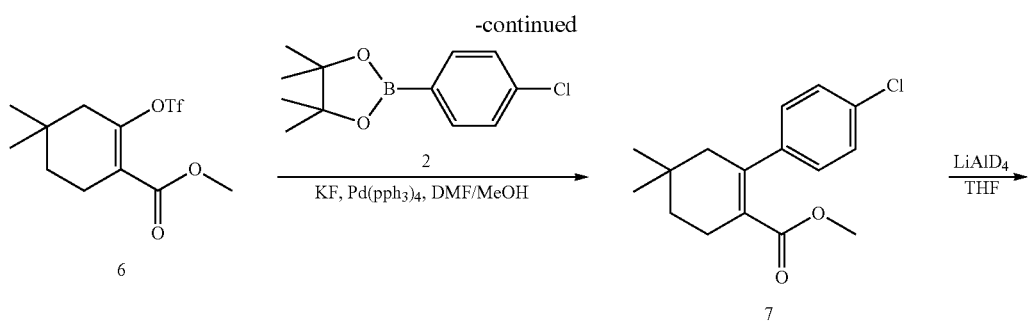
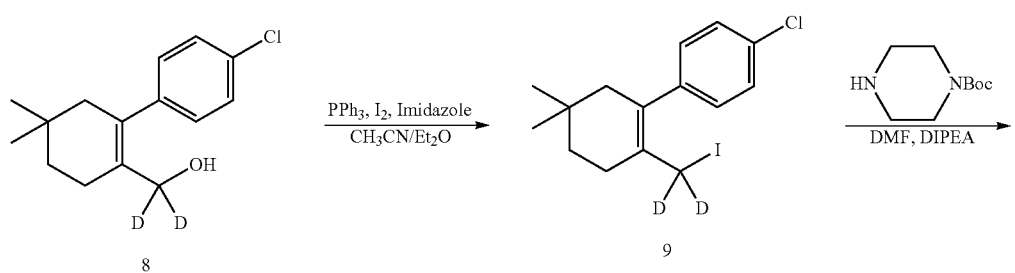
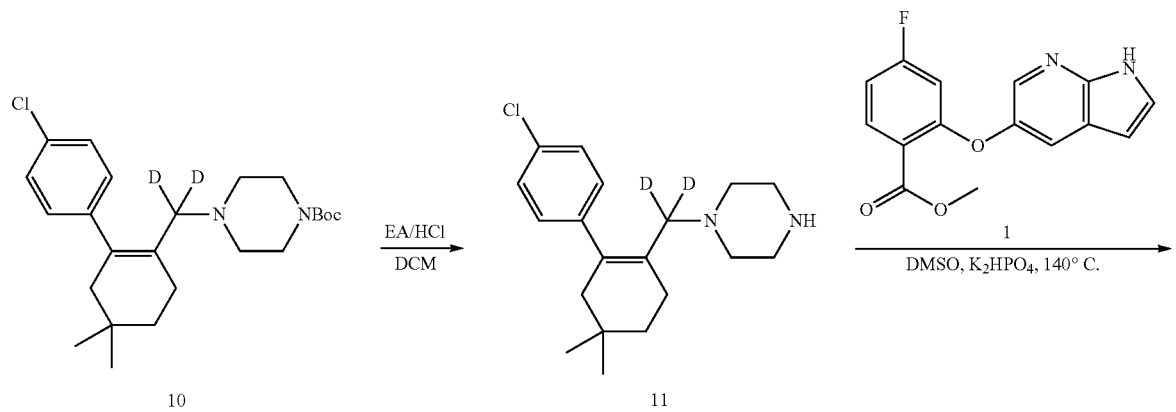
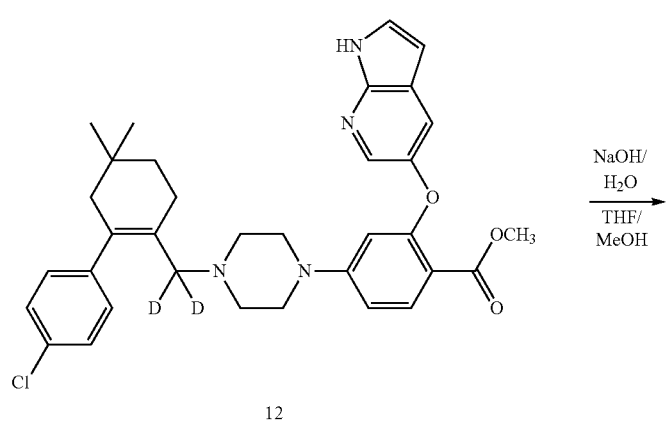

-continued

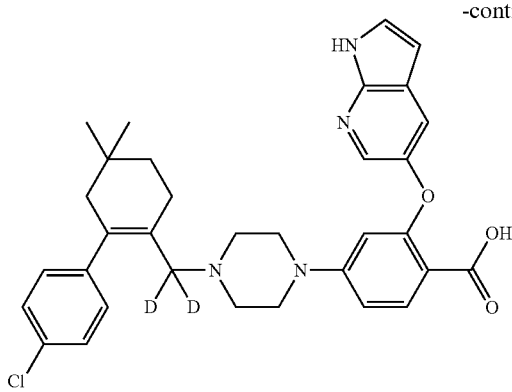

13

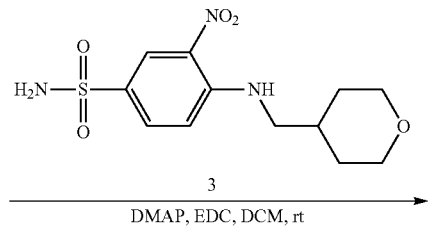

3
——————————→
DMAP, EDC, DCM, rt

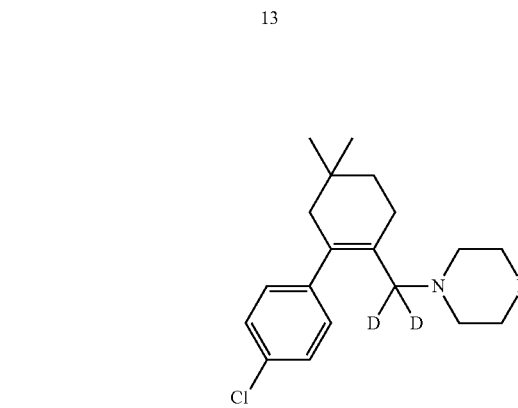

T-1

Step 1 Synthesis of Compound 5

Under the protection of nitrogen, sodium hydride (1.9 g, 79.3 mmol) and dimethyl carbonate (14.3 g, 158.6 mmol) were added to anhydrous THF (15 ml) and heated. A solution of 3,3-dimethylcyclohexan-1-one (5.0 g, 39.6 mmol) in THF was added dropwise while refluxing, and the refluxing was continued for 4 h after the addition. The mixture was cooled to room temperature and the reaction was quenched by the addition of methanol. Water and dichloromethane were added for extraction, and the organic phase was collected and purified by column chromatography to give 4.2 g of a colorless liquid product, with the yield of 70%.

Step 2 Synthesis of Compound 6

At 0° C., compound 5 (4.2 g, 22.8158.6 mmol) was added dropwise to a solution of sodium hydride (1.0 g, 45.6 mmol) in dichloromethane (80 mL) slowly. The mixture was reacted for 0.5 h and cooled to −25° C. Then trifluoromethanesulfonic anhydride (Tf$_2$O, 7.7 g, 27.4 mmol) was slowly added dropwise to the mixture, after which, the reaction solution was reacted overnight at room temperature. 2 M of ammonium chloride (50 ml) solution was added for extraction and the organic phase was collected, which was washed with water (60 ml×2) and dried over anhydrous sodium sulfate. The solvent was removed, and the concentrate was separated by column chromatography (eluent: petroleum ether/ethyl acetate (v/v)=100:1) to give 5.0 g of a light yellow liquid product, with the yield of 69%. $^1$H NMR (400 MHz, CDCl$_3$) δ 3.81 (s, 3H), 2.55-2.47 (m, 2H), 2.18 (t, J=2.4 Hz, 2H), 1.44 (t, J=6.4 Hz, 2H), 1.01 (s, 6H).

Step 3 Synthesis of Compound 7

Under the protection of nitrogen, compound 2 (0.70 g, 2.93 mmol), compound 6 (0.928 g, 2.93 mmol), tetrakis (triphenylphosphine)palladium (0.300 g, 0.29 mmol) and potassium fluoride (0.42 g, 7.33 mmol) were added to a mixture of dichloromethane (20 ml) and methanol (10 ml) successively, and the resulting mixture was heated to 65° C. for reaction for 6 h. After cooling to room temperature, the reaction was quenched with water (20 ml). Dichloromethane (30 ml×3) was added for extraction, and the organic phases were combined and dried over anhydrous sodium sulfate. The solvent was removed, and the concentrate was separated by column chromatography (eluent: petroleum ether/ethyl acetate (v/v)=40:1) to give 0.54 g of a colorless liquid product, with the yield of 67%. $^1$H NMR (400 MHz, CDCl$_3$) δ 7.33-7.27 (m, 2H), 7.06 (d, J=8.5 Hz, 2H), 3.49 (s, 3H), 2.53-2.45 (m, 2H), 2.15 (t, J=2.3 Hz, 2H), 1.51 (t, J=6.5 Hz, 2H), 1.02 (s, 6H).

Step 4 Synthesis of Compound 8

Under the condition of 0° C., LiAlD$_4$ (0.2 g, 5.02 mmol) was slowly added dropwise to a solution of compound 7 (0.7 g, 2.51 mmol) in tetrahydrofuran (20 ml), after which the reaction was continued for 1 h. 1 M of hydrochloric acid (10 ml) was added to quench the reaction, and the resulting mixture was extracted with dichloromethane (40 ml×3). The organic phases were combined and dried over anhydrous sodium sulfate. The solvent was removed to give 0.6 g of a light yellow liquid product, with the yield of 96%.

Step 5 Synthesis of Compound 9

A solution of compound 8 (1.2 g, 4.78 mmol) in mixture of acetonitrile (15 ml) and diethyl ether (15 ml) was cooled to −5° C. Imidazole (0.72 g, 10.53 mmol) and triphenylphosphine (2.5 g, 9.57 mmol) were added, and iodine (2.92 g, 11.51 mmol) was added slowly after the complete dissolution. The reaction was continued for 1 h, and water (20 ml) was added to quench the reaction. The resulting mixture was extracted with ethyl acetate (40 ml×2). The organic phases were combined and dried over anhydrous sodium sulfate. The solvent was removed, and the concentrate was separated by column chromatography (eluent: petroleum ether/ethyl acetate (v/v)=50:1) to give 1.3 g of a colorless liquid product, with the yield of 77%.

Step 6 Synthesis of Compound 10

Compound 9 (1.2 g, 3.33 mmol), N-tert-butoxycarbonyl-piperazine (0.74 g, 4.00 mmol) and N, N-diisopropylethylamine (DIPEA, 0.86 g, 6.66 mmol) were added to N, N-dimethylformamide (DMF, 10 ml) solution successively. The resulting mixture was heated to 80° C. and reacted for 1 h. The resulting mixture was cooled to room temperature and water (20 ml) was added to quench the reaction. Ethyl acetate (20 ml×3) was added for extraction, and the organic phases were combined and dried over anhydrous sodium sulfate. The solvent was removed, and the concentrate was separated by column chromatography (eluent: petroleum ether/ethyl acetate (v/v)=30:1) to give 1 μg of a product, with the yield of 79%.

Step 7 Synthesis of Compound 11

At 0° C., a solution of 4 M HCl in ethyl acetate (6 ml) was added to a solution of compound 10 (1.0 g, 2.40 mmol) in dichloromethane (15 ml) slowly, and the reaction was continued for 3 hours after being warmed to room temperature. After filtration, the filter cake was dissolved in water and neutralized with potassium phosphate. Ethyl acetate (30 ml×2) was added for extraction, and the organic phases were combined and dried over anhydrous sodium sulfate. The solvent was removed to give 0.7 g of a product, with the yield of 92%. LC-MS(APCI): m/z=322.13 (M+1)$^+$.

Step 8 Synthesis of Compound 12

Under the protection of nitrogen, compound 11 (0.9 g, 2.83 mmol), compound 1 (0.8 g, 2.83 mmol) and dipotassium hydrogen phosphate (0.98 g, 5.66 mmol) were added to dimethyl sulfoxide (DMSO, 25 ml) successively. The reaction solution was reacted at 140° C. for 12 h, and cooled to room temperature. Then water (50 ml) was added to quench the reaction. Ethyl acetate (40 ml×3) was added for extraction, and the organic phases were combined and dried over anhydrous sodium sulfate. The solvent was removed, and the concentrate was separated by column chromatography (eluent: petroleum ether/ethyl acetate (v/v)=3:1) to give 1.3 g of a yellow oil, with the yield of 78%. LC-MS(APCI): m/z=588.16 (M+1)$^+$.

Step 9 Synthesis of Compound 13

Sodium hydroxide (0.27 g, 6.85 mmol) and water (2 ml) were added to a mixed solution of compound 12 (0.8 g, 1.37 mmol) in tetrahydrofuran (10 ml) and methanol (3 ml). The reaction solution was stirred at 45° C. for 10 h and cooled to room temperature. Most of the solvent was removed, and the residue was adjusted to pH 2 with 2 M hydrochloric acid. Dichloromethane (30 ml×3) was added for extraction, and the organic phases were combined and dried over anhydrous sodium sulfate. The solvent was removed to give 0.65 g of a white solid, with the yield of 83%. $^1$H NMR (400 MHz, DMSO) δ 11.72 (s, 1H), 10.87 (s, 1H), 8.00 (d, J=2.6 Hz, 1H), 7.78 (d, J=8.9 Hz, 1H), 7.51-7.47 (m, 1H), 7.45 (d, J=2.5 Hz, 1H), 7.40 (d, J=8.5 Hz, 2H), 7.11 (d, J=8.4 Hz, 2H), 6.77 (dd, J=9.0, 2.4 Hz, 1H), 6.45-6.37 (m, 2H), 3.69 (d, J=13.2 Hz, 2H), 3.55 (d, J=4.1 Hz, 2H), 3.28 (d, J=12.3 Hz, 2H), 2.72 (d, J=11.6 Hz, 2H), 2.38 (s, 2H), 2.02 (s, 2H), 1.44 (t, J=6.1 Hz, 2H), 0.94 (s, 6H).

Step 10 Synthesis of Compound T-1

Compound 13 (0.10 g, 0.18 mmol), compound 3 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to the dichloromethane (20 ml) successively and the resulting mixture was stirred at room temperature for 10 h. Water (10 ml) was added to quench the reaction, and dichloromethane (15 ml×3) was added for extraction. The organic phases were combined and dried over anhydrous sodium sulfate. The solvent was removed, and the concentrate was separated by column chromatography (eluent: ethyl acetate/methanol (v/v)=30:1) to give 80 mg of a yellow solid, with the yield of 53%. LC-MS(APCI): m/z=871.36 (M+1)$^+$. $^1$H NMR (400 MHz, DMSO-d$_6$) δ 11.71 (s, 1H), 11.48 (s, 1H), 8.60-8.50 (m, 2H), 8.00 (dd, J=15.2, 5.6 Hz, 2H), 7.76 (d, J=9.0 Hz, 1H), 7.50 (t, J=6.1 Hz, 3H), 7.34 (d, J=8.4 Hz, 2H), 7.26 (d, J=8.6 Hz, 1H), 7.04 (d, J=8.3 Hz, 3H), 6.66 (d, J=8.9 Hz, 1H), 3.84 (dd, J=11.2, 2.9 Hz, 2H), 3.26 (dd, J=14.6, 8.7 Hz, 4H), 3.10 (s, 4H), 2.81 (s, 2H), 2.21 (d, J=34.6 Hz, 6H), 1.61 (d, J=11.5 Hz, 2H), 1.38 (t, J=6.2 Hz, 2H), 1.23 (s, 3H), 0.92 (s, 6H).

Example 2 Preparation of 4-(4-{[2-(4-chlorophenyl)-4,4-dimethylcyclohex-1-en-1-yl]methyl-d$_2$}piperazin-1-yl)-N-({3-nitro-4-[(tetrahydro-2H-pyran-4-ylmethyl-d$_2$)amino]phenyl}sulfonyl)-2-(1H-pyrrolo[2,3-b]pyridin-5-yloxy)benzamide, which is compound T-2, Represented by the Following Formula
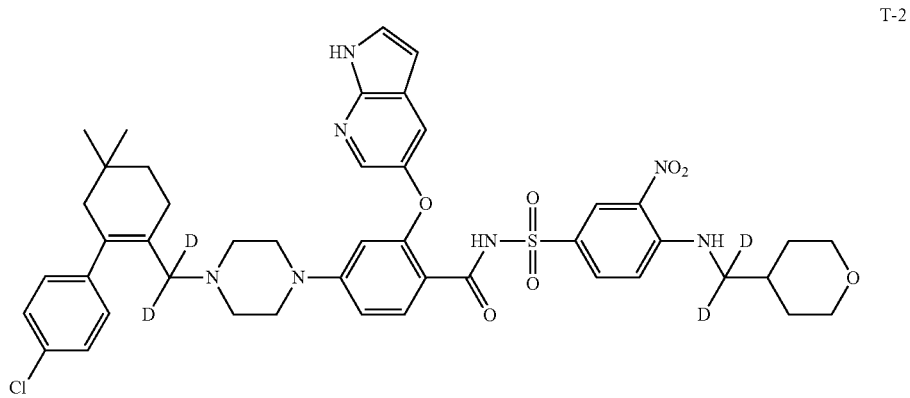 [SMILES: [2H]C([2H])(Nc1ccc(S(=O)(=O)NC(=O)c2ccc(N3CCN(C([2H])([2H])C4=C(c5ccc(Cl)cc5)CC(C)(C)CC4)CC3)cc2Oc2cnc3[nH]ccc3c2)cc1[N+](=O)[O-])C1CCOCC1]
The following routes is used for synthesis:
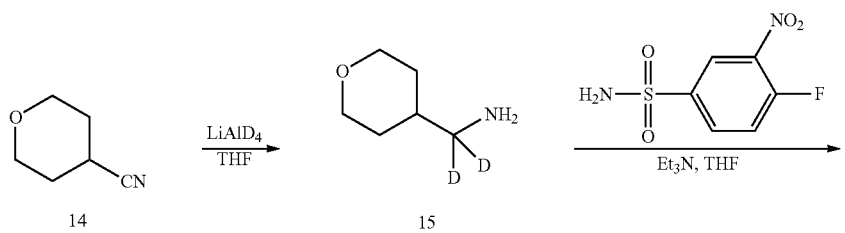
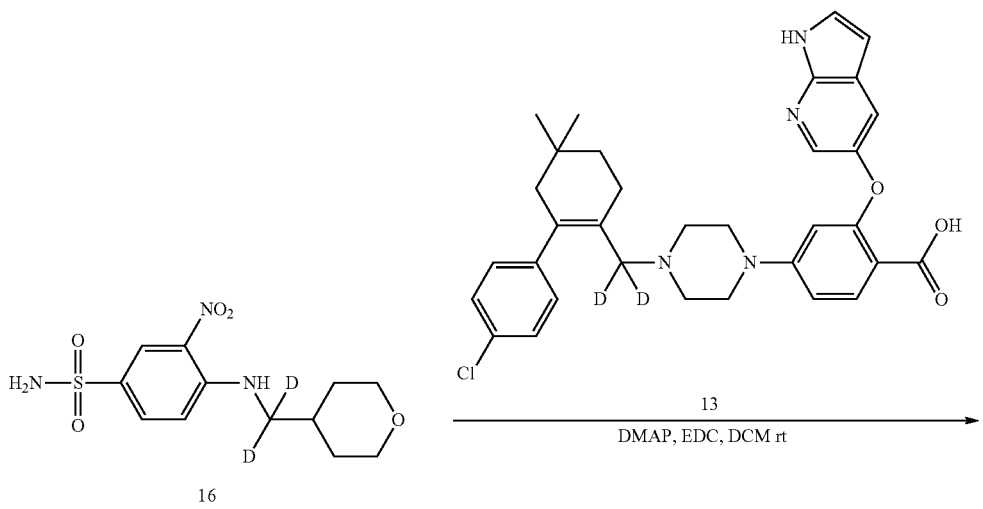

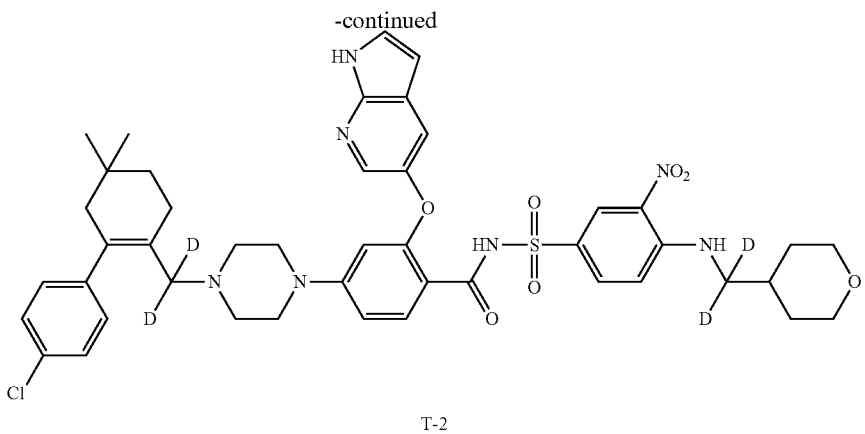

T-2

Step 1 Synthesis of Compound 15

Under the condition of 0° C., LiAlD$_4$ (0.4 g, 10.08 mmol) was added dropwise to a solution of compound 14 (1.0 g, 9.00 mmol) in tetrahydrofuran (20 ml) slowly, after which the reaction was continued for 1 h. 1 M of hydrochloric acid (10 ml) was added to quench the reaction, and the resulting mixture was extracted with dichloromethane (40 ml×3). The organic phases were combined and dried over anhydrous sodium sulfate. The solvent was removed to give 0.72 g of a light yellow solid, with the yield of 68.6%. LC-MS(APCI): m/z=118.29 (M+1)$^+$.

Step 2 Synthesis of Compound 16

4-Fluoro-3-nitrobenzenesulfonamide (1.12 g, 5.12 mmol), compound 15 (0.6 g, 5.12 mmol) and triethylamine (0.78 g, 7.68 mmol) were added to tetrahydrofuran (10 ml) successively. The reaction solution was stirred at room temperature for 5 h, and the solvent was removed. Methanol (10 ml) was added to form a slurry and the mixture was dried to give 0.8 g of a product, with the yield of 50%. LC-MS (APCI): m/z=318.20 (M+1)$^+$.

Step 3 Synthesis of Compound T-2

Compound 16 (0.056 g, 0.18 mmol), compound 13 (0.10 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to dichloromethane (20 ml) successively and the resulting mixture was stirred at room temperature for 10 h. Water (10 ml) was added to quench the reaction and dichloromethane (15 ml×3) was added for extraction. The organic phases were combined and dried over anhydrous sodium sulfate. The solvent was removed, and the concentrate was separated by column chromatography (eluent: ethyl acetate/methanol (v/v)=30:1) to give 45 mg of a yellow solid, with the yield of 30%. LC-MS(APCI): m/z=873.47 (M+1)$^+$. $^1$H NMR (400 MHz, DMSO-d$_6$) δ 11.71 (s, 1H), 11.49 (s, 1H), 8.56 (m, 2H), 8.00 (dd, J=5.2 Hz, 2H), 7.76 (d, J=9.0 Hz, 1H), 7.51 (t, J=6.1 Hz, 3H), 7.36 (d, J=8.4 Hz, 2H), 7.26 (d, J=8.2 Hz, 1H), 7.14 (d, J=8.3 Hz, 3H), 6.60 (d, J=8.9 Hz, 1H), 3.45-3.26 (dd, 4H), 3.10 (s, 4H), 2.81 (s, 2H), 2.56-2.21 (d, J=4.6 Hz, 6H), 1.61 (d, J=11.5 Hz, 2H), 1.38 (t, J=6.2 Hz, 2H), 1.23 (s, 3H), 0.92 (s, 6H).

Example 3 Preparation of 4-(4-{[2-(4-chlorophenyl)-4,4-dimethylcyclohex-1-en-1-yl]methyl}piperazin-1-yl)-N-({3-nitro-4-[(tetrahydro-2H-pyran-4-ylmethyl-d$_2$)amino]phenyl}sulfonyl)-2-(1H-pyrrolo[2,3-b]pyridin-5-yloxy)benzamide, which is compound T-3, Represented by the Following Formula

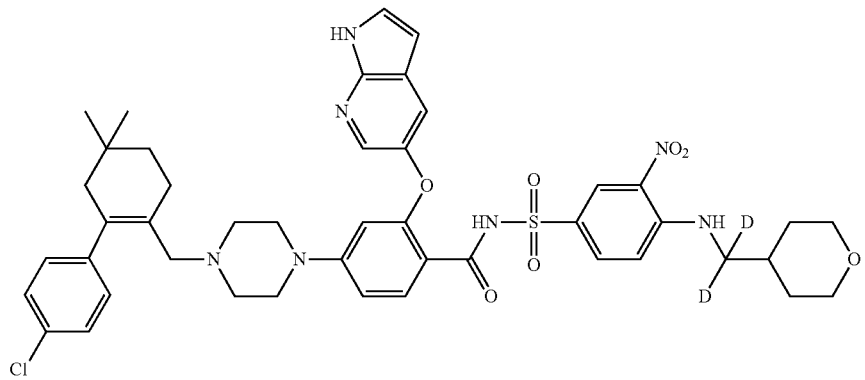

T-3

The following routes is used for synthesis:
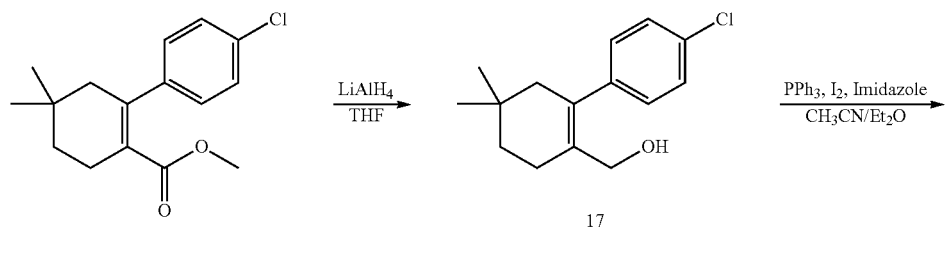
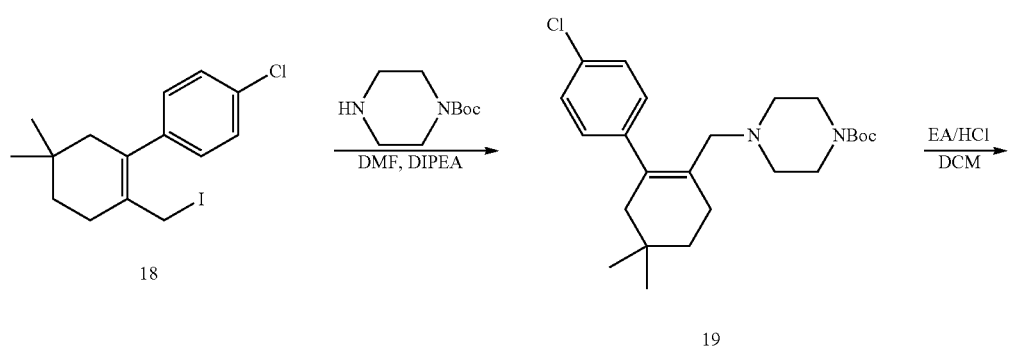
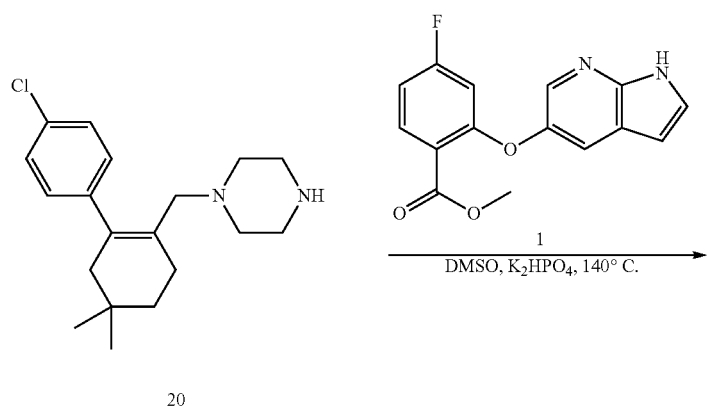
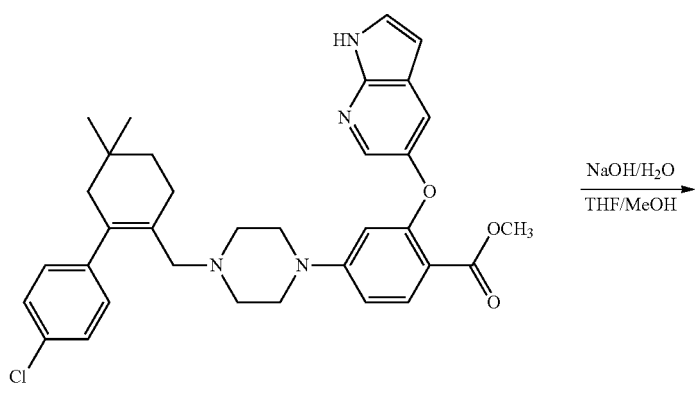

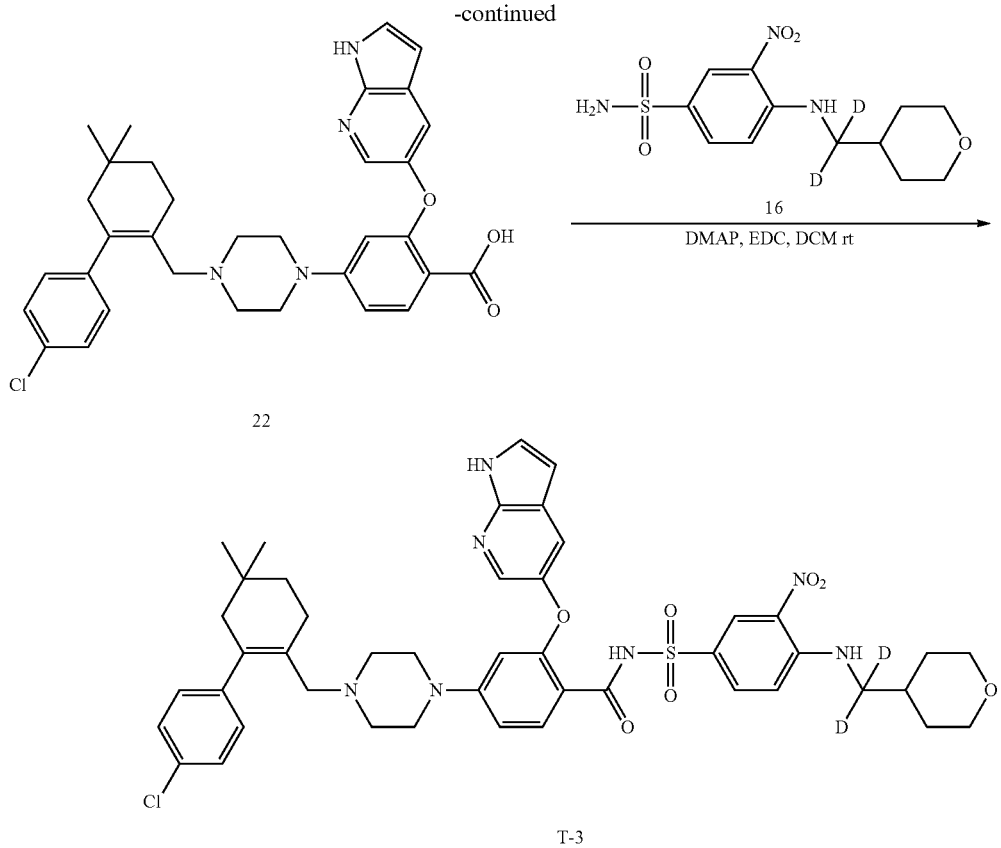

Step 1 Synthesis of Compound 17

Under the condition of 0° C., LiAlH$_4$ (0.14 g, 3.59 mmol) was added dropwise to a solution of compound 7 (1.0 g, 3.59 mmol) in tetrahydrofuran (20 ml) slowly, after which the reaction was continued for 1 h. 1 M of hydrochloric acid (10 ml) was added to quench the reaction, and the resulting mixture was extracted with dichloromethane (40 ml×3). The organic phases were combined and dried over anhydrous sodium sulfate. The solvent was removed to give 0.8 g of a light yellow liquid product, with the yield of 89%.

Step 2 Synthesis of Compound 18

Compound 17 (0.8 g, 3.19 mmol) was added to a mixture of acetonitrile (15 ml) and diethyl ether (15 ml) solution and the resulting mixture was cooled to −5° C. Imidazole (0.48 g, 7.01 mmol) and triphenylphosphine (1.67 g, 6.38 mmol) were added, and iodine (1.95 g, 7.65 mmol) was added slowly after the complete dissolution. The reaction was continued for 1 h, and water (20 ml) was added to quench the reaction. The resulting mixture was extracted with ethyl acetate (40 ml×2). The organic phases were combined and dried over anhydrous sodium sulfate. The solvent was removed, and the concentrate was separated by column chromatography (eluent: petroleum ether/ethyl acetate (v/v)=50:1) to give 0.9 g of a colorless liquid product, with the yield of 78%.

Step 3 Synthesis of Compound 19

Compound 18 (0.6 g, 1.67 mmol), N-tert-butoxycarbonyl-piperazine (0.37 g, 2.00 mmol) and N,N-diisopropylethyl-amine (DIPEA, 0.43 g, 3.33 mmol) were added to N,N-dimethylformamide (DMF, 10 ml) solution successively. The resulting mixture was heated to 80° C. and reacted for 1 h. The resulting mixture was cooled to room temperature and water (20 ml) was added to quench the reaction. Ethyl acetate (20 ml×3) was added for extraction, and the organic phases were combined and dried over anhydrous sodium sulfate. The solvent was removed, and the concentrate was separated by column chromatography (eluent: petroleum ether/ethyl acetate (v/v)=30:1) to give 0.6 g of a product, with the yield of 85%.

Step 4 Synthesis of Compound 20

At 0° C., a solution of 4 M HCl in ethyl acetate (4 ml) was added to a solution of compound 19 (0.6 g, 1.44 mmol) in dichloromethane (15 ml) slowly, and the reaction was continued for 3 h after being warmed to room temperature. After filtration, the filter cake was dissolved in water and neutralized with potassium phosphate. Ethyl acetate (30 ml×2) was added for extraction, and the organic phases were combined and dried over anhydrous sodium sulfate. The solvent was removed to give 0.4 g of a product, with the yield of 87%. LC-MS(APCI): m/z=319.87 (M+1)$^+$.

Step 5 Synthesis of Compound 21

Under the protection of nitrogen, compound 20 (1.0 g, 3.13 mmol), compound 1 (0.9 g, 3.13 mmol) and dipotassium hydrogen phosphate (1.10 g, 6.26 mmol) were added to dimethyl sulfoxide (DMSO, 25 ml) successively. The reaction solution was reacted at 140° C. for 12 h, and cooled to room temperature. Then water (50 ml) was added to quench the reaction. Ethyl acetate (50 ml×3) was added for extraction, and the organic phases were combined and dried over anhydrous sodium sulfate. The solvent was removed, and the concentrate was separated by column chromatography (eluent: petroleum ether/ethyl acetate (v/v)=3:1) to give 1.4 g of a yellow oil, with the yield of 76%. LC-MS(APCI): m/z=585.91 (M+1)⁺.

Step 6 Synthesis of Compound 22

Sodium hydroxide (0.20 g, 5.12 mmol) and water (2 ml) were added to a mixed solution of compound 21 (0.6 g, 1.03 mmol) in tetrahydrofuran (10 ml) and methanol (3 ml) successively. The reaction solution was stirred at 45° C. for 10 h and cooled to room temperature. Most of the solvent was removed, and the residue was adjusted to pH 2 with 2 M hydrochloric acid. Dichloromethane (30 ml×3) was added for extraction, and the organic phases were combined and dried over anhydrous sodium sulfate. The solvent was removed to give 0.45 g of a white solid, with the yield of 85%. LC-MS(APCI): m/z=572.11 (M+1)⁺.

Step 7 Synthesis of compound T-3

Compound 22 (0.10 g, 0.18 mmol), compound 16 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to dichloromethane (20 ml) successively and the resulting mixture was stirred at room temperature for 10 h. Water (10 ml) was added to quench the reaction. Dichloromethane (15 ml×3) was added for extraction, and the organic phases were combined and dried over anhydrous sodium sulfate. The solvent was removed, and the concentrate was separated by column chromatography (eluent: ethyl acetate/methanol (v/v)=30:1) to give 50 mg of a yellow solid, with the yield of 33%. ¹H NMR (400 MHz, DMSO-d₆) δ 11.70 (s, 1H), 11.45 (s, 1H), 8.62-8.51 (m, 2H), 8.00 (dd, J=18.9, 5.6 Hz, 2H), 7.78 (d, J=9.4 Hz, 1H), 7.54-7.45 (m, 3H), 7.34 (d, J=8.4 Hz, 2H), 7.26 (d, J=8.6 Hz, 1H), 7.06 (dd, J=17.2, 8.7 Hz, 3H), 6.67 (d, J=7.2 Hz, 1H), 6.38 (dd, J=3.2, 1.8 Hz, 1H), 6.20 (s, 1H), 3.84 (dd, J=11.2, 3.2 Hz, 2H), 3.09 (s, 4H), 2.79 (s, 2H), 2.20 (d, J=3.7 Hz, 5H), 1.95 (s, 2H), 1.61 (d, J=12.3 Hz, 2H), 1.38 (t, J=6.2 Hz, 2H), 1.23 (s, 2H), 0.92 (s, 6H).

Example 4 Preparation of 4-(4-{[2-(4-chlorophenyl)-4,4-dimethylcyclohex-1-en-1-yl]-methyl-d₂}piperazin-1-yl-2,2,3,3,5,5,6,6-d₈)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, which is compound T-4, Represented by the Following Formula

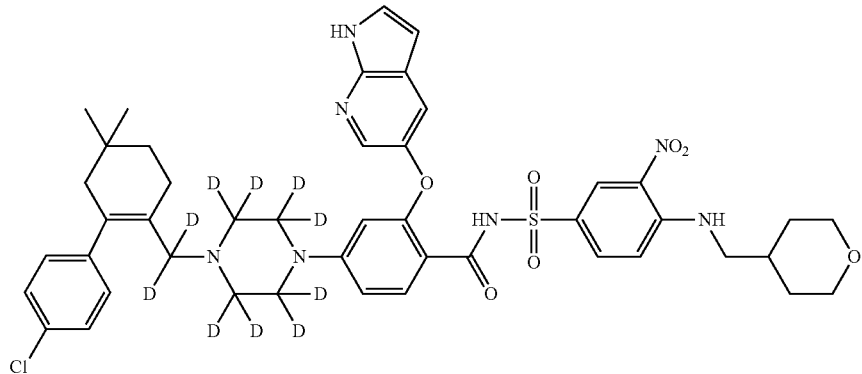

T-4

The following routes is used for synthesis:

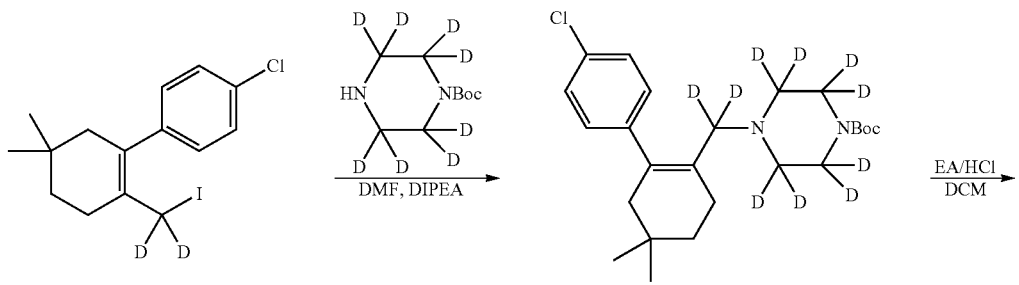

-continued
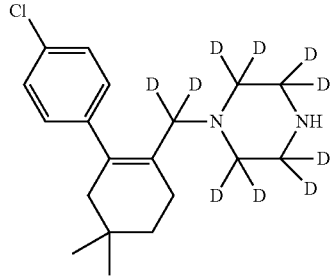 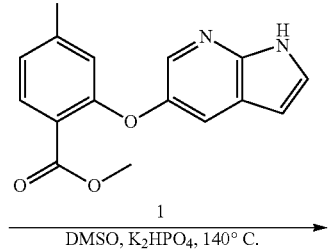
24
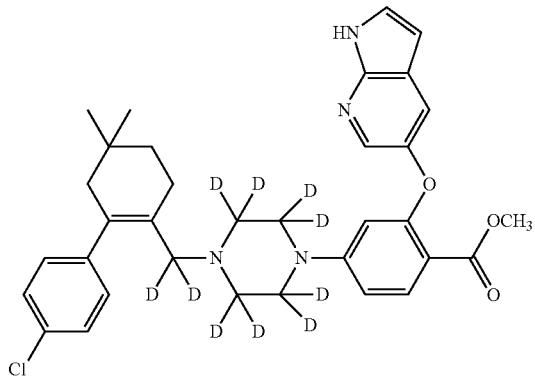
25
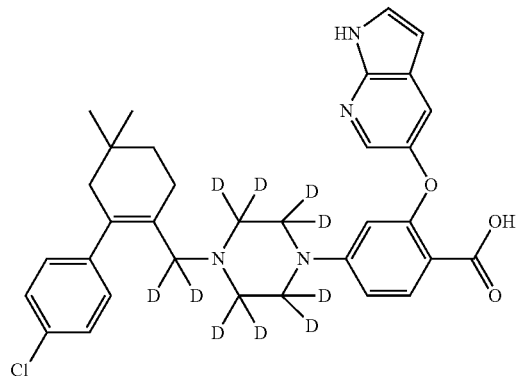 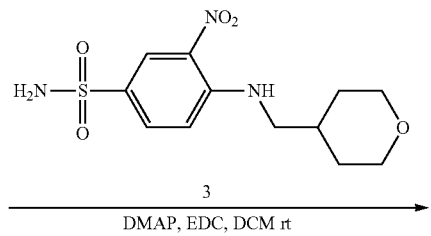
26
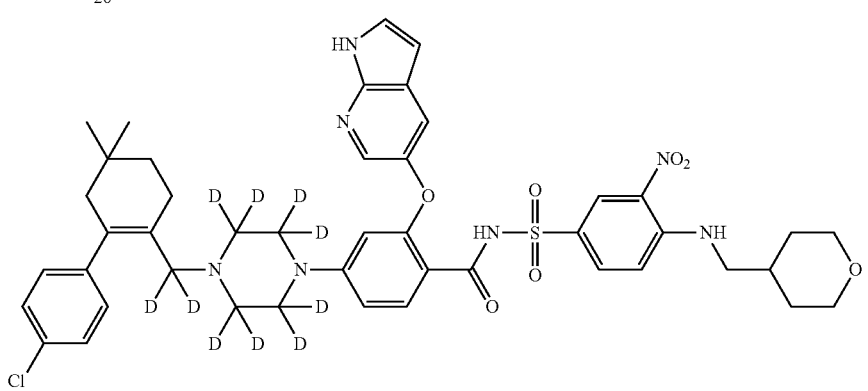
T-4

Step 1 Synthesis of Compound 23

Compound 9 (1.0 g, 2.76 mmol), N-tert-butoxycarbonyl-piperazin-2,2,3,3,5,5,6,6-$d_8$ (0.64 g, 3.31 mmol) and N,N-diisopropylethylamine (DIPEA, 0.54 g, 4.13 mmol) were added to N, N-dimethylformamide (DMF, 10 ml) successively. The resulting mixture was heated to 80° C. and reacted for 1 h. The resulting mixture was cooled to room temperature and water (20 ml) was added to quench the reaction. Ethyl acetate (20 ml×3) was added for extraction, and the organic phases were combined and dried over anhydrous sodium sulfate. The solvent was removed, and the concentrate was separated by column chromatography (eluent: petroleum ether/ethyl acetate (v/v)=30:1) to give 0.8 g of a product, with the yield of 68%.

Step 2 Synthesis of Compound 24

At 0° C., a solution of 4 M HCl in ethyl acetate (6 ml) was added to a solution of compound 23 (0.8 g, 1.86 mmol) in dichloromethane (15 ml) slowly, and the reaction was continued for 3 h after being warmed to room temperature. After filtration, the filter cake was dissolved in water and neutralized with potassium phosphate. Ethyl acetate (30 ml×2) was added for extraction, and the organic phases were combined and dried over anhydrous sodium sulfate. The solvent was removed to give 0.7 g of a product, with the yield of 92%. LC-MS(APCI): m/z=329.41 (M+1)$^+$.

Step 3 Synthesis of Compound 25

Under the protection of nitrogen, compound 24 (0.5 g, 1.52 mmol), compound 1 (0.44 g, 1.52 mmol) and dipotassium hydrogen phosphate (0.53 g, 3.04 mmol) were added to dimethyl sulfoxide (DMSO, 15 ml) successively. The reaction solution was reacted at 140° C. for 12 h, and cooled to room temperature. Then water (30 ml) was added to quench the reaction. Ethyl acetate (40 ml×3) was added for extraction, and the organic phases were combined and dried over anhydrous sodium sulfate. The solvent was removed, and the concentrate was separated by column chromatography (eluent: petroleum ether/ethyl acetate (v/v)=3:1) to give 0.62 g of a yellow oil, with the yield of 69%. LC-MS(APCI): m/z=596.39 (M+1)$^+$.

Step 4 Synthesis of Compound 26

Sodium hydroxide (0.21 g, 5.04 mmol) and water (2 ml) were added to a mixed solution of compound 25 (0.6 g, 1.01 mmol) in tetrahydrofuran (10 ml) and methanol (3 ml) successively. The reaction solution was stirred at 45° C. for 10 h and cooled to room temperature. Most of the solvent was removed, and the residue was adjusted to pH 2 with 2 M hydrochloric acid. Dichloromethane (30 ml×3) was added for extraction, and the organic phases were combined and dried over anhydrous sodium sulfate. The solvent was removed to give 0.48 g of a white solid, with the yield of 82%.

Step 5 Synthesis of Compound T-4

Compound 26 (0.10 g, 0.18 mmol), compound 3 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to the dichloromethane (20 ml) successively and the resulting mixture was stirred at room temperature for 10 h. Water (10 ml) was added to quench the reaction. Dichloromethane (15 ml×3) was added for extraction, and the organic phases were combined and dried over anhydrous sodium sulfate. The solvent was removed, and the concentrate was separated by column chromatography (eluent: ethyl acetate/methanol (v/v)=30:1) to give 90 mg of a yellow solid, with the yield of 59%. LC-MS(APCI): m/z=878.92 (M+1)$^+$. $^1$H NMR (400 MHz, DMSO-$d_6$) δ 11.72 (s, 1H), 11.43 (s, 1H), 8.71-8.50 (m, 2H), 8.10 (dd, J=15.6, 5.6 Hz, 2H), 7.76 (d, J=9.0 Hz, 1H), 7.60 (t, J=6.1 Hz, 3H), 7.34 (d, J=8.4 Hz, 2H), 7.16 (d, J=8.6 Hz, 1H), 7.04 (d, J=8.3 Hz, 3H), 6.51 (d, J=8.9 Hz, 2H), 3.84 (dd, 2H), 3.26 (dd, J=8.7 Hz, 2H), 3.10 (s, 2), 2.81 (s, 2H), 2.35 (d, 2H), 1.61 (d, J=11.5 Hz, 2H), 1.38 (t, J=6.2 Hz, 2H), 1.21 (s, 2H), 0.94 (s, 6H).

Example 5 Preparation of 4-(4-{[2-(4-chlorophenyl)-4,4-dimethylcyclohex-1-en-1-yl]methyl}piperazin-1-yl-2,2,3,3,5,5,6,6-$d_8$)-N-({3-nitro-4-[(tetrahydro-2H-pyran-4-ylmethyl)amino]phenyl}sulfonyl)-2-(1H-pyrrolo[2,3-b]pyridin-5-yloxy)benzamide, which is compound T-5, Represented by the Following Formula

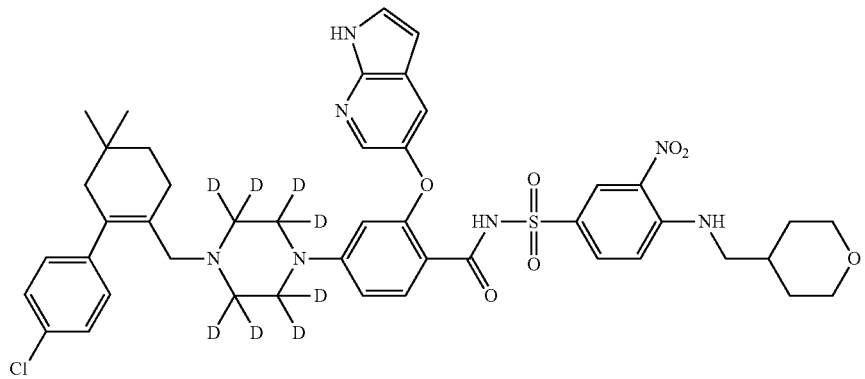

T-5

The following routes is used for synthesis:
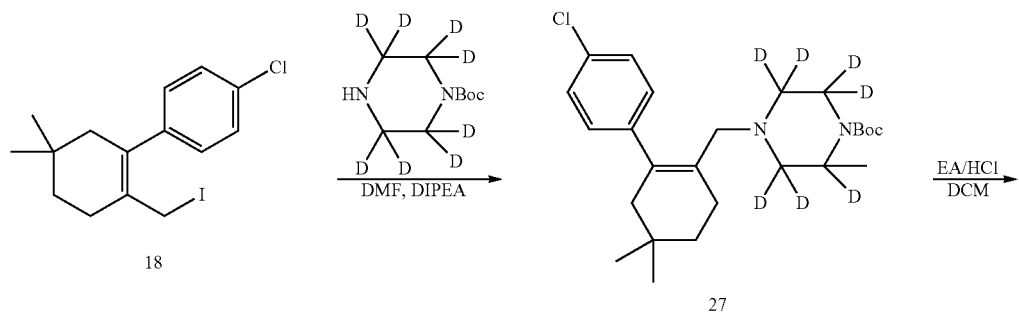
18
27
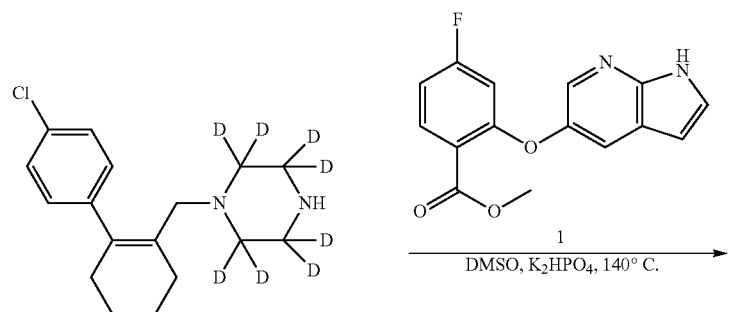
28
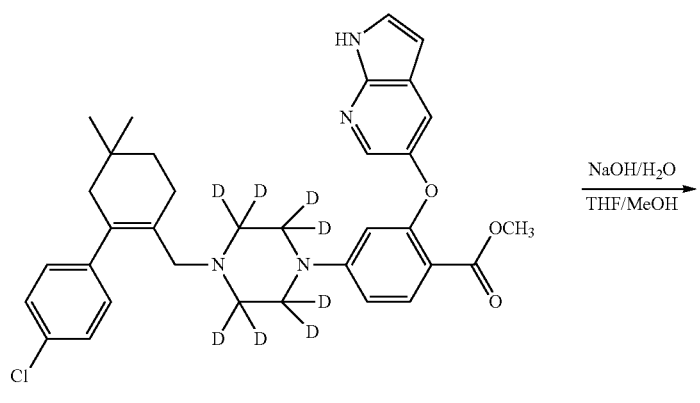
29
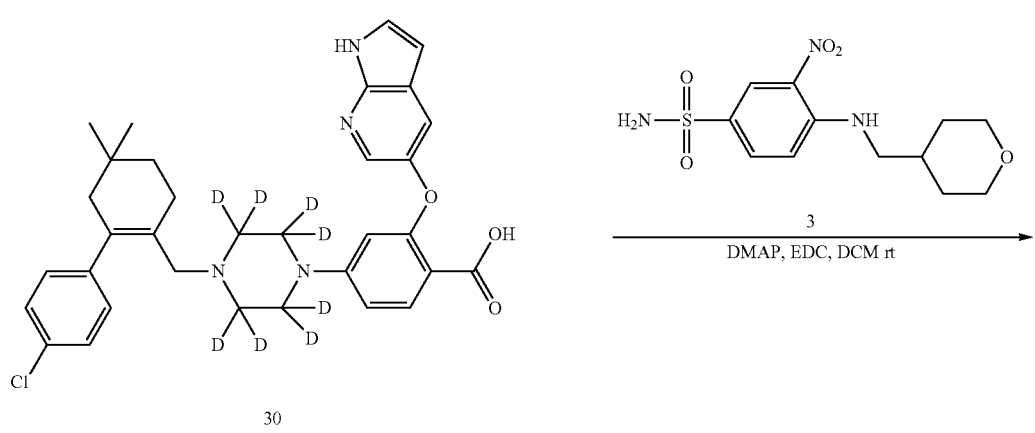
30

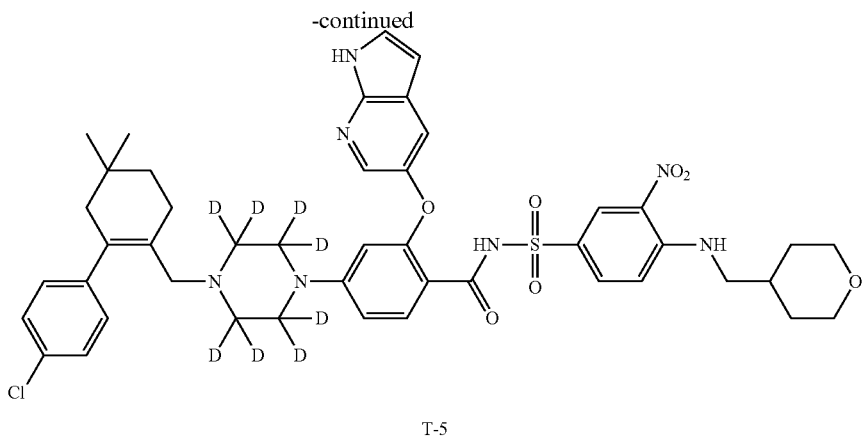

T-5

Step 1 Synthesis of Compound 27

Compound 18 (1.3 g, 3.60 mmol), N-tert-butoxycarbonyl-piperazin-2,2,3,3,5,5,6,6-$d_8$ (0.70 g, 3.60 mmol) and N,N-diisopropylethylamine (DIPEA, 0.70 g, 5.40 mmol) were added to N,N-dimethylformamide (DMF, 10 ml) successively. The resulting mixture was heated to 80° C. and reacted for 1 h. The resulting mixture was cooled to room temperature and water (20 ml) was added to quench the reaction. Ethyl acetate (30 ml×3) was added for extraction, and the organic phases were combined and dried over anhydrous sodium sulfate. The solvent was removed, and the concentrate was separated by column chromatography (eluent: petroleum ether/ethyl acetate (v/v)=30:1) to give 1.2 g of a product, with the yield of 78%.

Step 2 Synthesis of Compound 28

At 0° C., a solution of 4 M HCl in ethyl acetate (6 ml) was added to a solution of compound 27 (1.2 g, 2.81 mmol) in dichloromethane (15 ml) slowly, and the reaction was continued for 3 h after being warmed to room temperature. After filtration, the filter cake was dissolved in water and neutralized with potassium phosphate. Ethyl acetate (30 ml×2) was added for extraction, and the organic phases were combined and dried over anhydrous sodium sulfate. The solvent was removed to give 0.8 g of a product, with the yield of 87%. LC-MS(APCI): m/z=327.26 (M+1)$^+$.

Step 3 Synthesis of Compound 29

Under the protection of nitrogen, compound 28 (0.8 g, 2.45 mmol), compound 1 (0.70 g, 2.45 mmol) and dipotassium hydrogen phosphate (0.64 g, 3.67 mmol) were added to dimethyl sulfoxide (DMSO, 15 ml) successively. The reaction solution was reacted at 140° C. for 12 h, and cooled to room temperature. Then water (30 ml) was added to quench the reaction. Ethyl acetate (50 ml×3) was added for extraction, and the organic phases were combined and dried over anhydrous sodium sulfate. The solvent was removed, and the concentrate was separated by column chromatography (eluent: petroleum ether/ethyl acetate (v/v)=3:1) to give 1.21 g of a yellow oil, with the yield of 83%. LC-MS(APCI): m/z=594.09 (M+1)$^+$.

Step 4 Synthesis of Compound 30

Sodium hydroxide (0.34 g, 8.43 mmol) and water (2 ml) were added to a mixed solution of compound 29 (1.0 g, 1.69 mmol) in tetrahydrofuran (10 ml) and methanol (3 ml). The reaction solution was stirred at 45° C. for 10 h and cooled to room temperature. Most of the solvent was removed, and the residue was adjusted to pH 2 with 2 M hydrochloric acid. Dichloromethane (30 ml×3) was added for extraction, and the organic phases were combined and dried over anhydrous sodium sulfate. The solvent was removed to give 0.70 g of a white solid, with the yield of 71%.

Step 5 Synthesis of Compound T-5

Compound 30 (0.10 g, 0.18 mmol), compound 3 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to the dichloromethane (20 ml) successively and the resulting mixture was stirred at room temperature for 10 h. Water (10 ml) was added to quench the reaction. Dichloromethane (15 ml×3) was added for extraction, and the organic phases were combined and dried over anhydrous sodium sulfate. The solvent was removed, and the concentrate was separated by column chromatography (eluent: ethyl acetate/methanol (v/v)=30:1) to give 55 mg of a yellow solid, with the yield of 36%. LC-MS(APCI): m/z=876.85 (M+1)$^+$. $^1$H NMR (400 MHz, DMSO-$d_6$) δ 11.72 (s, 1H), 11.43 (s, 1H), 8.76-8.50 (m, 2H), 8.17 (dd, J=5.6 Hz, 2H), 7.76 (d, J=9.0 Hz, 1H), 7.60 (t, J=6.1 Hz, 3H), 7.34 (d, J=8.4 Hz, 2H), 7.16 (d, J=8.6 Hz, 1H), 7.04 (d, J=8.3 Hz, 3H), 6.51 (d, J=8.9 Hz, 2H), 3.85 (dd, 2H), 3.57 (dd, 2H), 3.26 (dd, J=8.7 Hz, 2H), 3.10 (s, 2), 2.81 (s, 2H), 2.35 (d, 2H), 1.63 (d, 2H), 1.38-1.19 (m, 4H), 0.94 (s, 6H).

Example 6 Preparation of 4-(4-{[2-(4-chlorophenyl)-4,4-dimethylcyclohex-1-en-1-yl]methyl}piperazin-1-yl-2,2,3,3,5,5,6,6-d$_8$)-N-({3-nitro-4-[(tetrahydro-2H-pyran-4-ylmethyl-d$_2$)amino]phenyl}sulfonyl)-2-(1H-pyrrolo[2,3-b]pyridin-5-yloxy)benzamide, which is compound T-6, Represented by the Following Formula
T-6
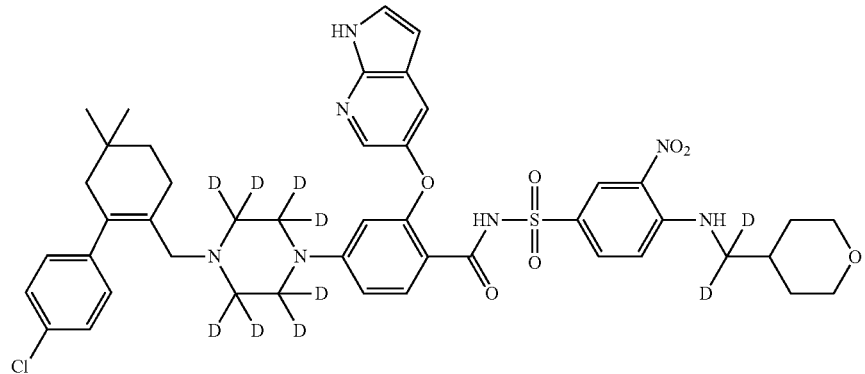
The following routes is used for synthesis:
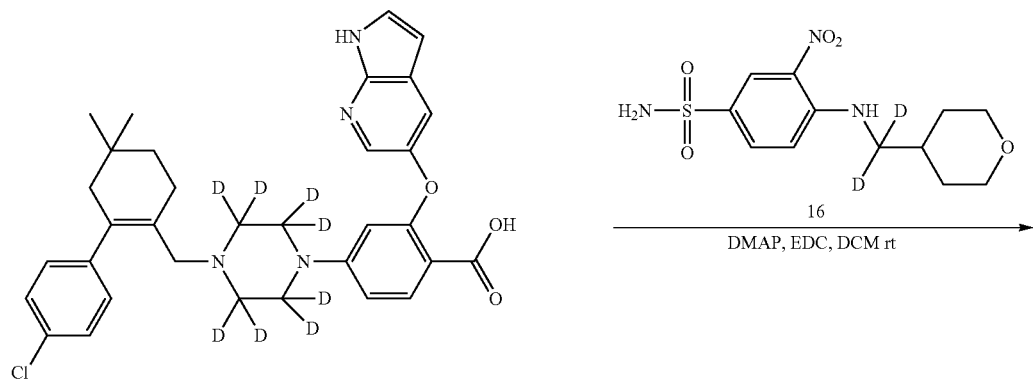
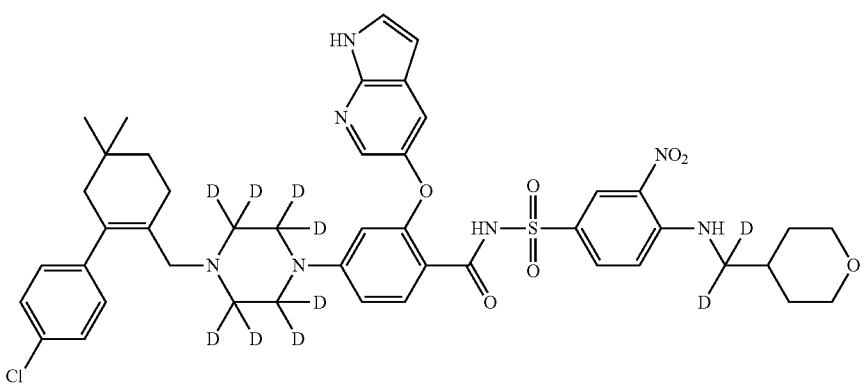
T-6

Compound 30 (0.10 g, 0.18 mmol), compound 16 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to the dichloromethane (20 ml) successively and the resulting mixture was stirred at room temperature for 10 h. Water (10 ml) was added to quench the reaction. Dichloromethane (15 ml×3) was added for extraction, and the organic phases were combined and dried over anhydrous sodium sulfate. The solvent was removed, and the concentrate was separated by column chromatography (eluent: ethyl acetate/methanol (v/v)=30:1) to give 60 mg of a yellow solid, with the yield of 39%. LC-MS(APCI): m/z=878.79 (M+1)$^+$. $^1$H NMR (400 MHz, DMSO) δ 11.73 (s, 1H), 11.40 (s, 1H), 8.76-8.60 (m, 2H), 8.17 (dd, J=5.8 Hz, 2H), 7.82 (d, J=9.0 Hz, 1H), 7.60 (t, J=6.1 Hz, 3H), 7.34 (d, J=8.4 Hz, 2H), 7.16 (d, J=8.6 Hz, 2H), 7.04 (d, J=8.3 Hz, 2H), 6.51 (d, J=8.9 Hz, 2H), 3.87 (m, 2H), 3.57 (dd, 2H), 3.10 (s, 2), 2.81 (s, 2H), 2.35 (m, 2H), 1.63 (d, 2H), 1.38-1.16 (m, 4H), 0.96 (s, 6H).

Example 7 Preparation of 4-(4-{[2-(4-chlorophenyl)-4,4-dimethylcyclohex-1-en-1-yl]methyl-d$_2$}piperazin-1-yl-2,2,3,3,5,5,6,6-d$_8$)-N-({3-nitro-4-[(tetrahydro-2H-pyran-4-ylmethyl-d$_2$)amino]phenyl}sulfonyl)-2-(1H-pyrrolo[2,3-b]pyridin-5-yloxy)benzamide, which is compound T-7, Represented by the Following Formula

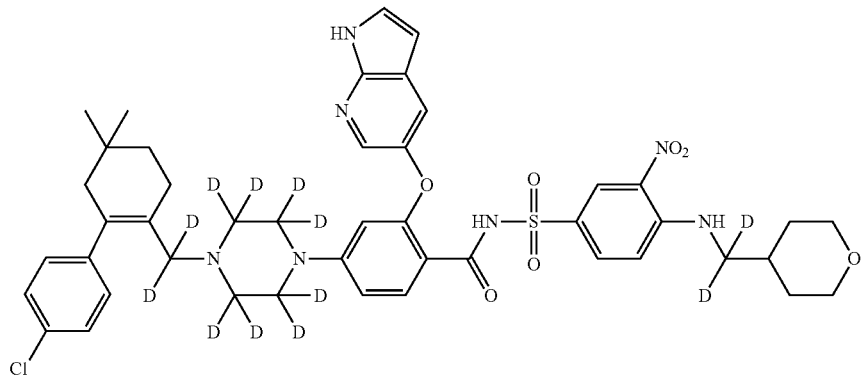

T-7

The following routes is used for synthesis:

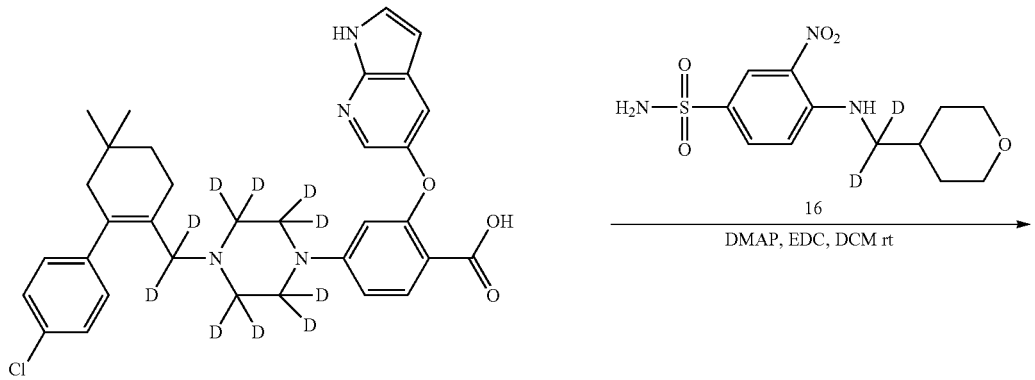

-continued

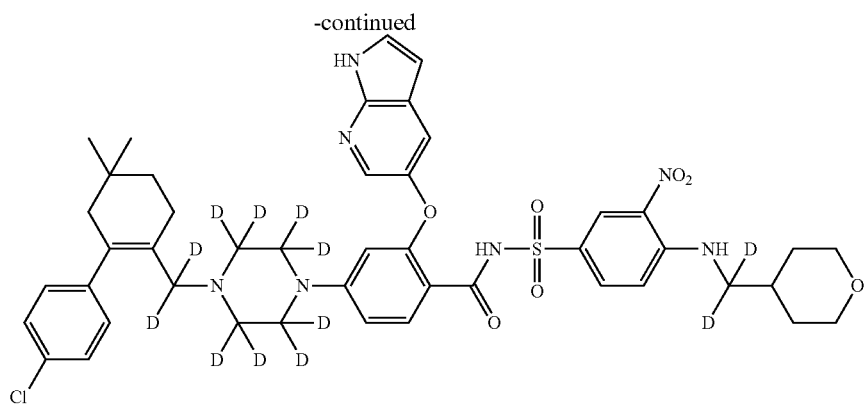

T-7

Compound 26 (0.10 g, 0.18 mmol), compound 16 (0.055 g, 0.18 mmol), 1-(3-dimethylaminopropyl)-3-ethylcarbodiimide hydrochloride (EDC, 0.052 g, 0.27 mmol) and 4-dimethylaminopyridine (DMAP, 0.044 mg, 0.36 mmol) were added to the dichloromethane (20 ml) successively and the resulting mixture was stirred at room temperature for 10 h. Water (10 ml) was added to quench the reaction. Dichloromethane (15 ml×3) was added for extraction, and the organic phases were combined and dried over anhydrous sodium sulfate. The solvent was removed, and the concentrate was separated by column chromatography (eluent: ethyl acetate/methanol (v/v)=30:1) to give 40 mg of a yellow solid, with the yield of 26%. LC-MS(APCI): m/z=880.52 (M+1)$^+$. $^1$H NMR (400 MHz, DMSO) δ 11.73 (s, 1H), 11.42 (s, 1H), 8.76-8.63 (m, 2H), 8.17 (dd, J=5.8 Hz, 2H), 7.82 (d, J=9.0 Hz, 1H), 7.60 (t, J=6.1 Hz, 3H), 7.34 (d, J=8.4 Hz, 2H), 7.16 (d, J=8.6 Hz, 2H), 7.04 (d, J=8.3 Hz, 2H), 3.87 (m, 2H), 3.57 (dd, 2H), 3.10 (s, 2), 2.81 (s, 2H), 2.35 (m, 4H), 1.63 (m, 2H), 1.38-1.16 (m, 2H), 0.95 (s, 6H).

Biological Activity Assay (1) Bcl-2 Protein Activity Assay

Proteins: Bcl-2 (Cisbio 63ADK000CB01PEG); Bcl-xL (Cisbio 63ADK000CB04PEG);

Experimental procedures: a) Dilution of the compounds in DMSO: the compounds to be tested (10 mM stock solutions) were diluted 500 times with DMSO as the first concentration, and the resulting solutions were diluted using a 3-fold serial dilution, resulting in a total of 10 concentration gradients, and the 11th concentration was DMSO control. b) 100 nL/well of the compounds (which were prepared in the step a) was added to a 384 reaction plate (6008280, PerkinElmer) using ECHO, and the plate was centrifugated at 1000 rpm for 1 minute for future use. c) 5 μL/well of BCL-2 solution (2 nM) and BCL-X1 (5 nM), respectively, was added to the 384 reaction plate added with compounds as described above, and the plate was centrifugated at 1000 rpm for 1 minute; to which 5 μL/well of BAK (80 nM) was added, and the plate was centrifugated at 1000 rpm for 1 minute and incubated at 25° C. for 15 minutes. The concentrations of the compounds were started from 100 nM as the initial concentration, and diluted with a 3-fold serial dilution to obtain 10 plus 0 points in total. The final concentration of DMSO was 0.5%. d) 10 μL/well of Anti-Tag1-Eu3+& Anti-Tag2-XL665 solution (cisbio) was added to the 384 reaction plate described above, and the plate was centrifugated at 1000 rpm for 1 minute, and incubated at 25° C. for 180 minutes. e) The ratio of 665/615 nm was read with a Envision Multi-function Reader. The inhibition constant (Ki) of the compounds of the present disclosure is determined in this manner, wherein the Ki of the compounds is expressed as "<" (less than) a specific value, meaning that the binding affinity value is lower than the detection limit of the test used. Wang's Competitive Binding of Two Different Ligands to a Protein Molecule. *FEBS Lett.* 1995,360:111-4 was used as a reference.

The inhibition constant (Ki) is the dissociation constant of an enzyme-inhibitor complex or a protein/small molecule complex, wherein the small molecule inhibits the binding of one protein to another protein or peptide. Therefore, a high Ki value indicates a low binding affinity, while a low Ki value indicates a high binding affinity.

Compounds of the present disclosure and Venetoclax were tested by the experimental procedures described above. Compared with the non-deuterated Venetoclax, compounds of the present disclosure have better binding affinity to the anti-apoptotic Bcl-2 protein, and have poor binding affinity to the Bcl-xL protein, showing a high selectivity for Bcl-2 protein. The specific experimental results are shown in Table 1 below.

TABLE 1

| Compounds of the examples | Bcl-2 (Ki nM) | Bcl-xL (Ki nM) |
| --- | --- | --- |
| Venetoclax | 0.90 | >100 |
| T-1 | 1.20 | >100 |
| T-2 | 1.03 | >100 |
| T-3 | 0.86 | >100 |
| T-4 | 0.88 | >100 |
| T-5 | 0.18 | >100 |
| T-6 | 1.71 | >100 |
| T-7 | 0.64 | >100 |

(2) Cell Viability Test

Acute lymphocytic leukemia (ALL) cell line RS4;11 was used as a primary human cell line to evaluate the cell viability of Bcl-2 selectors in vitro and their efficacy in vivo.

RS4;11 was cultured in RPMI-1640 supplemented with 2 mM L-glutamine, 10% FBS, 1 mM sodium pyruvate, 2 mM HEPES, 1% penicillin/streptomycin and 4.5 g/L glucose, and maintained at 37° C. in the environment of 5% carbon dioxide. In order to test the effect of the compounds on cellular viability in vitro, cells were treated in a 96-well microtiter plate with 50000 cells per well in the presence of 10% human serum for 48 hours in a humid room with 5% carbon dioxide. Cytotoxic $EC_{50}$ values were evaluated using CellTier Glo (Promega) according to the manufacturer's recommendations. The $EC_{50}$ value is determined by the percentage of viable cells after the treatment relative to untreated control cells.

The experimental results show that compounds of the present disclosure are very effective in inhibiting RS4;11 cells, and the specific experimental results are shown in Table 2 below.

TABLE 2

| Compounds of the examples | RS4; 11 (Ki nM) |
|---|---|
| Venetoclax | 3.07 |
| T-1 | 4.13 |
| T-2 | 4.29 |
| T-3 | 3.66 |
| T-4 | 2.93 |
| T-5 | 2.86 |
| T-6 | 6.74 |
| T-7 | 3.15 |

(3) Liver Microsomal Metabolism Experiment

Microsome assay: mouse liver microsomes: 0.5 mg/mL, Xenotech; coenzyme (NADPH/NADH): 1 mM, Sigma Life Science; magnesium chloride: 5 mM, 100 mM phosphate buffer (pH 7.4).

Preparation of stock solutions: Powder of the compounds were accurately weighed and dissolved in DMSO to 5 mM.

Preparation of phosphate buffer (100 mM, pH7.4): A pre-prepared 0.5M potassium dihydrogen phosphate (150 mL) was mixed with 0.5M dibasic potassium phosphate (700 mL). The pH of the mixture was adjusted to 7.4 with 0.5M dibasic potassium phosphate solution. The mixture was diluted 5-fold with ultrapure water before use, and magnesium chloride was added to obtain a phosphate buffer (100 mM) containing 100 mM potassium phosphate, 3.3 mM magnesium chloride, pH 7.4.

A NADPH regeneration system solution (containing 6.5 mM NADP, 16.5 mM G-6-P, 3 U/mL G-6-P D, 3.3 mM magnesium chloride) was prepared and placed on wet ice prior to use.

Preparation of stop solution: an acetonitrile solution containing 50 ng/mL propranolol hydrochloride and 200 ng/mL tolbutamide (internal standard). 25057.5 μL of phosphate buffer (pH 7.4) was taken into a 50 mL centrifuge tube, to which 812.5 μL mouse liver microsomes were added, and mixed to obtain a liver microsome dilution with a protein concentration of 0.625 mg/mL.

Incubation of the samples: The stock solutions of the respective compounds were respectively diluted to 0.25 mM with an aqueous solution containing 70% acetonitrile, and used as a working solution, ready for use. 398 μL of the dilution of human liver microsomes or rat mouse liver microsomes were added to 96-well incubation plates (N=2), respectively, and 2 μL of 0.25 mM working solution was added and mixed.

Metabolic stability assay: 300 μL of pre-chilled stop solution was added to each well of 96-well deep well plates and placed on ice as stop plates. The 96-well incubation plates and NADPH regeneration system were placed in a 37° C. water bath box, shaken at 100 rpm and pre-incubated for 5 min. 80 μL of incubation solution was taken out from each well of the incubation plates and added to the stop plates, mixed, and replenished with 20 μL of NADPH regeneration system solution as a 0-min sample. 80 μL of NADPH regeneration system solution was added to each well of the incubation plates to start the reaction and start counting. The corresponding compounds had a reaction concentration of 1 μM and the protein concentration was 0.5 mg/mL. Separately, 100 μL of the reaction solutions was taken at 10, 30, and 90 min reaction, respectively, added to stop plates, and vortexed for 3 minutes to terminate the reaction. The stop plates were centrifuged at 5000×g at 4° C. for 10 min. 100 μL of the supernatant was added to a 96-well plate to which 100 μL of distilled water was previously added, mixed, and analyzed by LC-MS/MS.

Data analysis: The peak areas of the corresponding compounds and internal standard were detected by LC-MS/MS system, and the ratio of the peak area of the compounds to the internal standard was calculated. The slope was measured by plotting the natural logarithm of the percent of compound remaining versus time, and $t_{1/2}$ and $CL_{int}$ were calculated according to the equation below, where V/M equals to 1/protein concentration.

$$t_{1/2} = -\frac{0.693}{\text{Slope}}, \quad CL_{int} = \frac{0.693}{t_{1/2}} \cdot \frac{V}{M}$$

The metabolic stability of the compounds in mouse liver microsomes was evaluated by simultaneously testing and comparing the compounds disclosed herein and the non-deuterated compound. The half-life and liver intrinsic clearance as indicators of metabolic stability are shown in Table 3. In Table 3, the non-deuterated compound Venetoclax was used as a control sample. As shown in Table 3, compared with the non-deuterated compound Venetoclax, the compounds of the present disclosure can significantly improve the metabolic stability, and thus are more suitable to be used as hepatitis C virus inhibitors.

TABLE 3

Comparison of metabolic stability between Examples 1 to 7 (which are, compounds T-1 to T-7) and Venetoclax control

| Compounds of the examples | Mouse liver microsome experiment | |
|---|---|---|
| | $t_{1/2}$ (min) | $CL_{int}$ (μL/min/mg) |
| Venetoclax | 81.1 | 17.1 |
| T-1 | 244.3 | 5.7 |
| T-2 | 142.7 | 9.7 |
| T-3 | 75.3 | 18.4 |
| T-4 | 67.1 | 20.7 |
| T-5 | 91.1 | 15.2 |
| T-6 | 77.8 | 17.8 |
| T-7 | 306.9 | 4.5 |

(4) Pharmacokinetic Experiment in Rats

Experimental Objective: To investigate the pharmacokinetic behavior of the compounds of the present disclosure after the rats being administered with the test compounds.

Experimental Animals:

Species and strain: SD rat grade: SPF grade

Gender and quantity: male, 6

Weight range: from 180 to 220 g (actual weight range is from 187 to 197 g)

Source: Shanghai Sippr-BK Laboratory Animal Co. Ltd.

Laboratory and Animal Qualification Certificate: SCXK (Shanghai) 2013-0016

Experimental procedures: Before blood samples were collected, 20 μL of 2 M sodium fluoride solution (esterase inhibitor) was previously added to an EDTA-K2 anticoagulant tube, dried in an 80° C. oven, and placed in a 4° C. refrigerator.

Rats (male, weighing 187 to 197 g) were randomly divided into 2 groups, and were fasted overnight in the afternoon before the experiment but were allowed to drink water freely. Food was given 4 hours after the administration. Group A was given Venetoclaxr (3 mg/kg), and group B was given example compounds 1 to 7 (3 mg/kg). About 100-200 μL of blood was taken from the orbital vein of rats at 15 min, 30 min, 1, 2, 3, 5, 8 and 10 h after administration, placed in a 0.5 mL Eppendorf tube with EDTA-K2 anticoagulant and mixed immediately. After anticoagulation, the tube was gently inverted 5-6 times as quickly as possible. After the blood was taken, it was placed in an ice box, and then within 30 min, the blood sample was centrifuged for 10 min at 4000 rpm and 4° C. to separate the plasma. Immediately after collection of all plasma, it was stored at −20° C. The concentration of the drug in plasma at each time point was determined after sample collection at all time points.

Based on the data of the average concentration of the drug in plasma versus time after administration obtained as described above, pharmacokinetics-related parameters of male SD rats after the i.g. administration of Venetoclax and representative example compounds (3 mg/kg) were calculated using the Winnonin software according to non-compartment statistical moment theory.

The experiments showed that, the compounds of the present disclosure have better pharmacokinetic properties compared to the non-deuterated compound. The specific experimental results are as follows:

| Compound Number | $T_{max}$ (h) | $C_{max}$ (ng/mL) | $AUC_{last}$ (h*ng/mL) | MRT (h) | $Cl_{\_pred}$ (L/h/kg) | F (%) |
|---|---|---|---|---|---|---|
| Venetoclax | 3.33 | 477.9 | 3060.7 | 5.22 | 3.28 | 3.47 |
| T-3 | 3.33 | 680.0 | 4425.2 | 5.07 | 2.41 | 7.10 |

It should be understood that these examples are only for illustrating the present disclosure and are not intended to limit the scope disclosed herein. Experimental methods that do not specify specific conditions in the examples are generally based on conventional conditions or conditions recommended by the manufacturer. Parts and percentages are parts by weight and percentages by weight unless otherwise indicated.

The above content is a further detailed description disclosed herein in combination with specific preferred embodiments, and it cannot be assumed that the specific implementation disclosed herein is limited to these descriptions. For a person of ordinary skill in the art to which the present disclosure belongs, a number of simple deductions or substitutions can be made without departing from the concept disclosed herein, and should all be considered as falling within the protection scope disclosed herein.

The invention claimed is:

1. A compound represented by formula (I), or a pharmaceutically acceptable salt, prodrug, crystal form, stereoisomer, hydrate or solvate thereof:

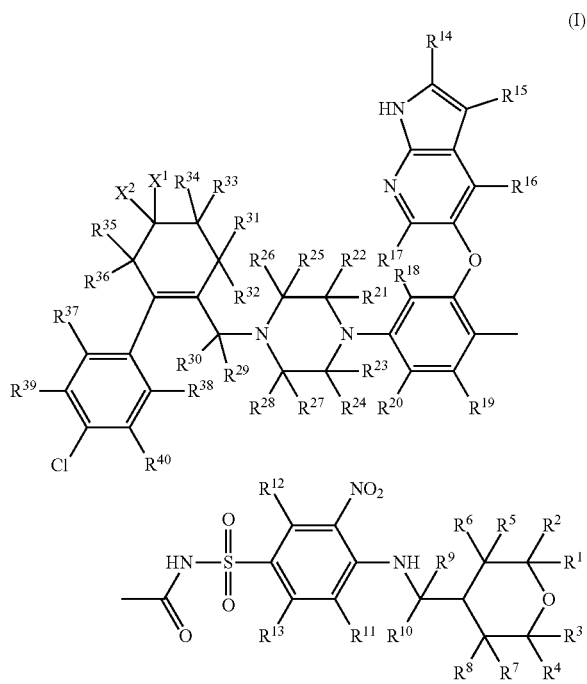

wherein, $R^1$, $R^2$, $R^3$, $R^4$, $R^5$, $R^6$, $R^7$, and $R^8$ are hydrogen;

$R^9$ and $R^{10}$ are deuterium;

$R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$ $R^{30}$, $R^{31}$, $R^{32}$, $R^{33}$, $R^{34}$, $R^{35}$, $R^{36}$, $R^{37}$, $R^{38}$, $R^{39}$ and $R^{40}$ are independently selected from hydrogen, deuterium, halogen and trifluoromethyl;

$X^1$ and $X^2$ are independently selected from the group consisting of hydrogen (H), deuterium (D), methyl, $CH_2D$, $CHD_2$, $CD_3$, $CH_2CH_3$, $CHDCH_3$, $CHDCH_2D$, $CHDCHD_2$, $CHDCD_3$, $CD_2CH_3$, $CD_2CH_2D$, $CD_2CHD_2$ and $CD_2CD_3$;

the content of deuterium isotope in each deuterated position is at least greater than 50%.

2. The compound according to claim 1, wherein $R^{31}$, $R^{32}$ $R^{33}$, $R^{34}$, $R^{35}$ and $R^{36}$ are hydrogen, and $X^1$ and $X^2$ are methyl.

3. The compound according to claim 2, wherein $R^{21}$, $R^{22}$, $R^{23}$, $R^{24}$, $R^{25}$, $R^{26}$, $R^{27}$ and $R^{28}$ are hydrogen.

4. The compound according to claim 1, which is selected from the compounds represented by the following formula:

(1)
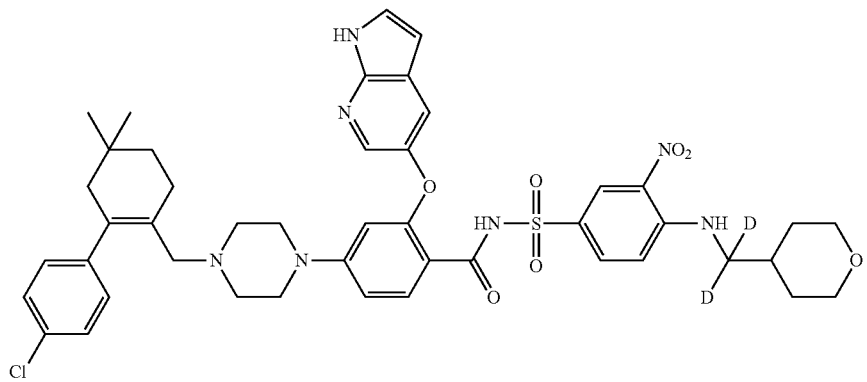
(20)
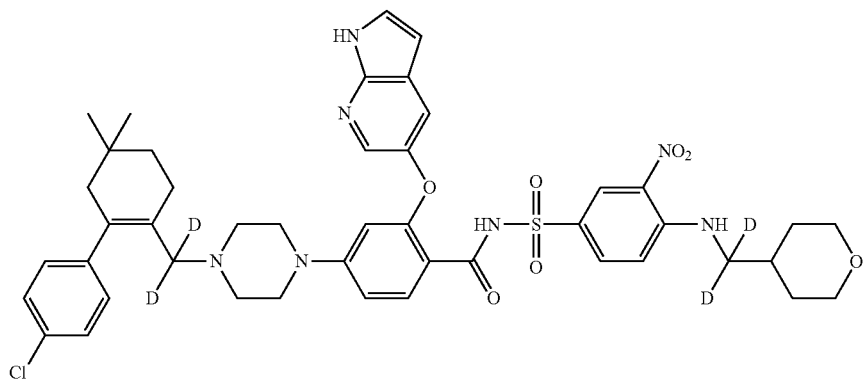
(21)
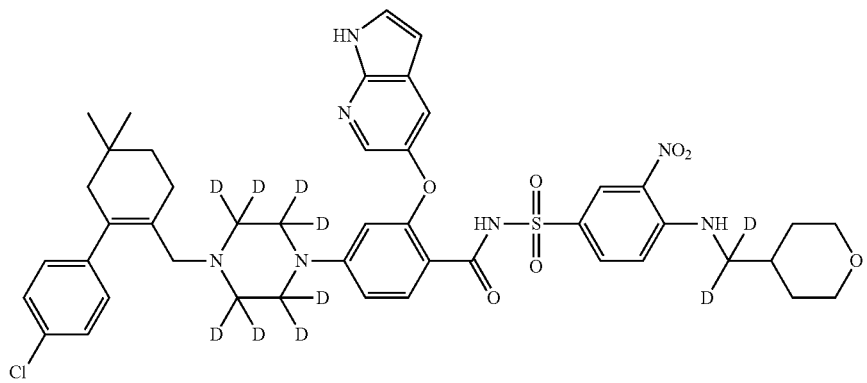
(22)
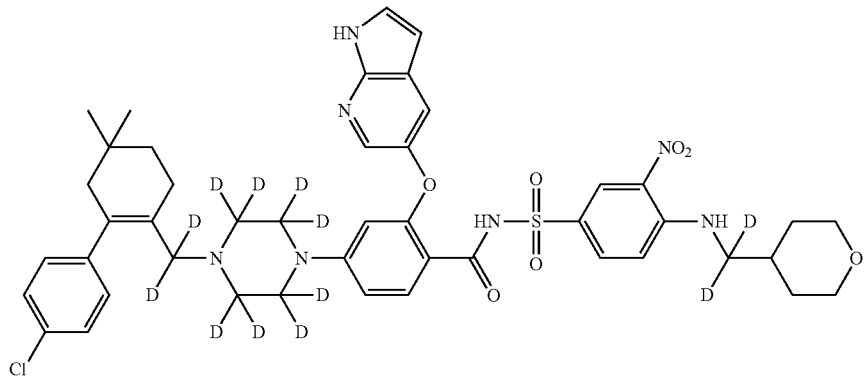

(25)
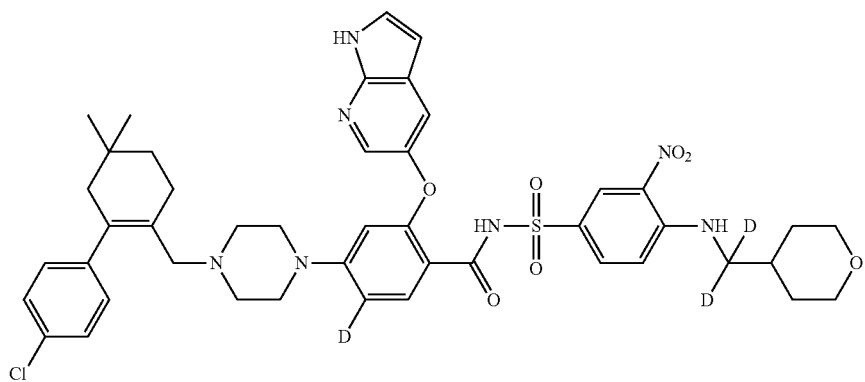
(27)
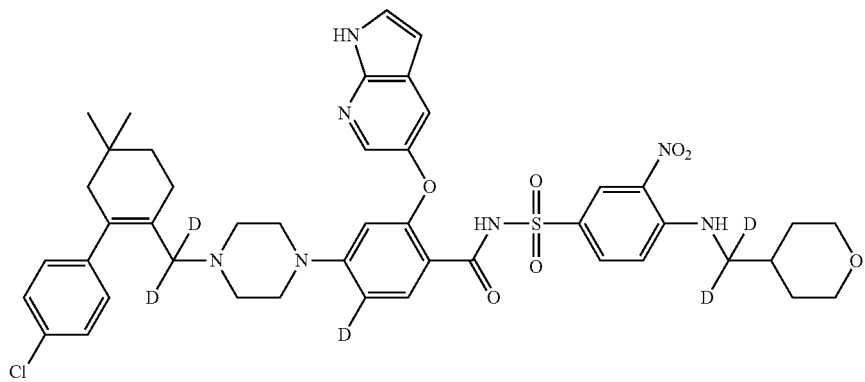
(28)
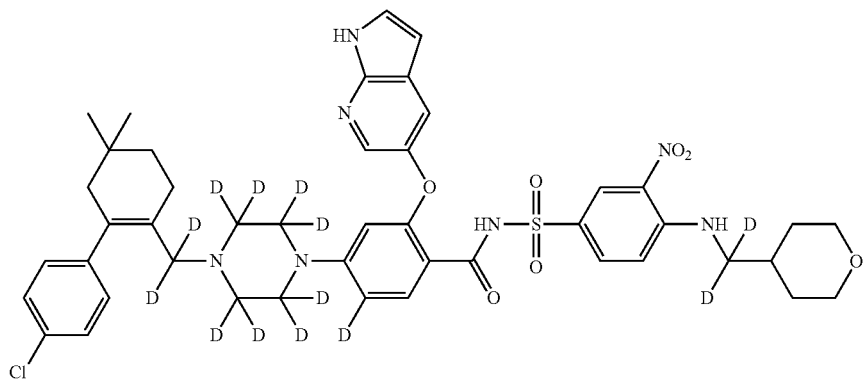
(29)
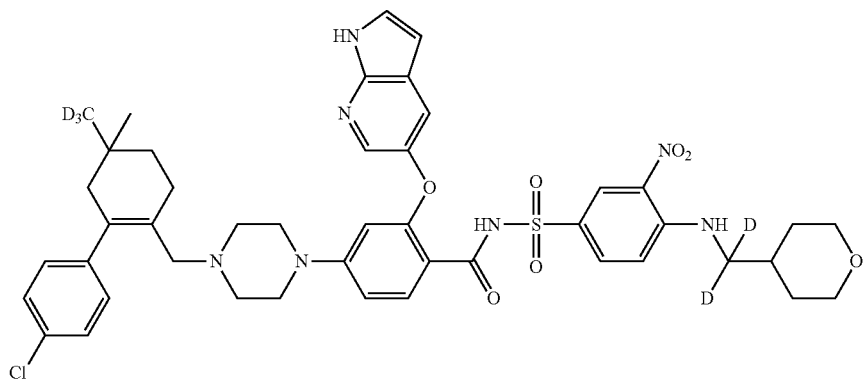

-continued
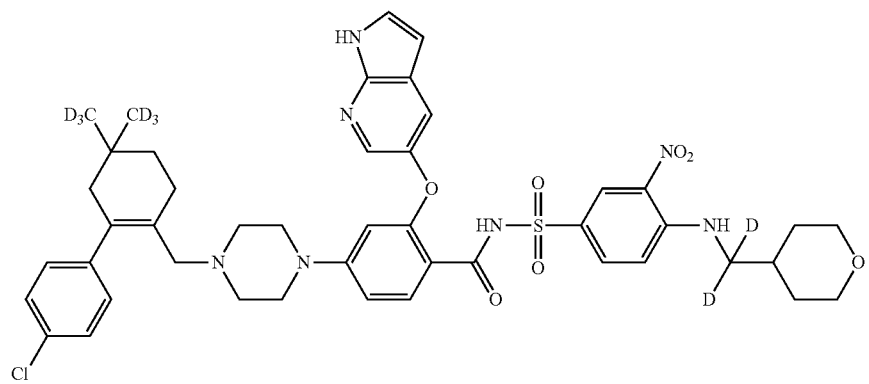
(30)
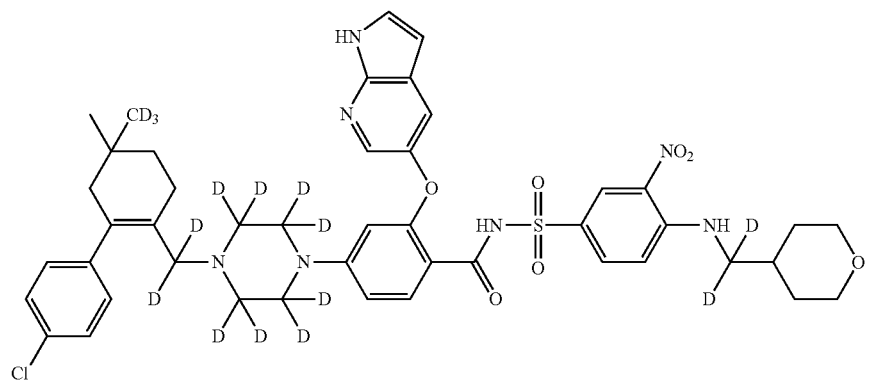
(33)
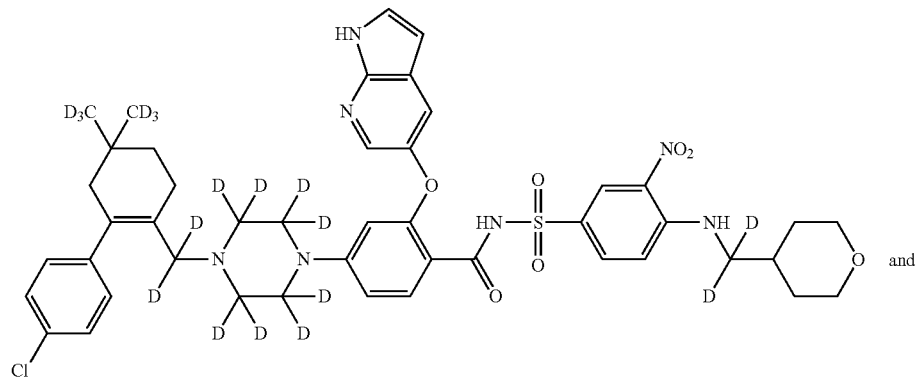
(34)
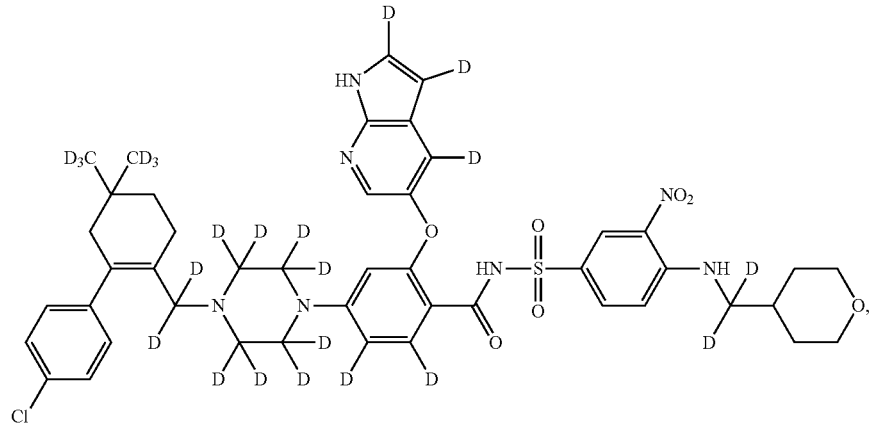
(35)
or a pharmaceutically acceptable salt thereof.

5. The compound according to claim 1, which is the following compound:

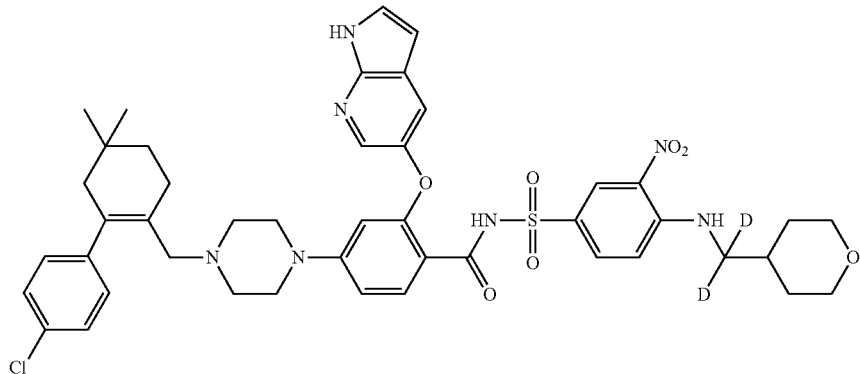

T-3 or a pharmaceutically acceptable salt thereof.

6. A pharmaceutical composition, comprising a pharmaceutically acceptable carrier and compound according to claim 1, or a crystal form, pharmaceutically acceptable salt, hydrate or solvate, stereoisomer, or prodrug thereof.

7. A pharmaceutical composition, comprising a pharmaceutically acceptable carrier and compound according to claim 4, or a pharmaceutically acceptable salt thereof.

8. A pharmaceutical composition, comprising a pharmaceutically acceptable carrier and compound according to claim 5, or a pharmaceutically acceptable salt thereof.

* * * * *